(12) United States Patent
Yue et al.

(10) Patent No.: US 7,022,507 B1
(45) Date of Patent: Apr. 4, 2006

(54) ISOLATED POLYNUCLEOTIDE ENCODING A HUMAN PSST SUBUNIT OF THE NADH:UBIQUINONE OXIDOREDUCTASE COMPLEX

(75) Inventors: Henry Yue, Sunnyvale, CA (US); Preeti Lal, Santa Clara, CA (US); Y. Tom Tang, San Jose, CA (US); Dyung Aina M. Lu, San Jose, CA (US); Janice Au-Young, Brisbane, CA (US)

(73) Assignee: Incyte Corporation, Wilmington, DE (US)

( * ) Notice: Subject to any disclaimer, the term of this patent is extended or adjusted under 35 U.S.C. 154(b) by 548 days.

(21) Appl. No.: 09/525,867

(22) Filed: Mar. 15, 2000

Related U.S. Application Data

(60) Provisional application No. 60/124,655, filed on Mar. 16, 1999.

(51) Int. Cl.
*C12N 9/02* (2006.01)
*C12N 15/00* (2006.01)
*C12N 5/00* (2006.01)
*C12N 1/20* (2006.01)
*C07H 2/104* (2006.01)

(52) U.S. Cl. .................. 435/189; 435/25; 435/69.1; 435/325; 435/252.3; 435/320.1; 536/23.2; 530/350

(58) Field of Classification Search ............... 435/25, 435/69.1, 189, 325, 252.3, 320.1; 536/23.2; 530/350
See application file for complete search history.

(56) References Cited

FOREIGN PATENT DOCUMENTS

| | | |
|---|---|---|
| EP | 0559428 B1 | 3/1993 |
| EP | 1033405 A2 | 2/2000 |
| WO | WO 99/40189 | 8/1999 |

OTHER PUBLICATIONS

Broun et al., Science 282:1315-1317, 1998.*
Van de Loo et al., Proc. Natl. Acad. Sci. 92:6743-6747, 1995.*
Hyslop et al., Genomics 37:375-380, 1996.*
Arizmendi et al., FEBS Lett. 301:237-242, 1992; Swiss Prot accession No. P42026, Nov. 1, 1995.*
Bork, Genome Research, 10:398-400, 2000.*
Seffernick et al., J. Bacteriol. 183(8):2405-2410, 2001.*
Witkowski et al., Biochemistry 38:11643-11650, 1999.*
Brenner, TIG 15:132-133, 1999.*
Darnell et al., Molecular Cell Biology, Scientific American Books, 1986.*
Avers, Genetics, 2nd edition, Willard Grand Press, 1984.*
Sakharkar et al., "distributions of exons and introns in the human genome," In Silco Biology, vol. 4, p. 0032 (Jun. 16, 2004).*
Hogue, D.L. et al., "Identification and Characterization of a Mammalian Mitochondrial ATP-binding Cassette Membrane Protein", *J. Mol. Biol.*, (1999) 285, 379-389.
Cannon, B. et al., "Brown Adipose Tissue More Than an Effector of Thermogenesis?", *Ann. N.Y. Acad. Sci.*, (Sep. 29, 1998) 856:171-87.
Lodish, H. et al., "Mitochondria and the Metabolism of Carbohydrates and Lipids", *Molecular Cell Biology*, 3d ed. (1995) pp. 745-752.
Pfanner, N., "Uniform nomenclature for the protein transport machinery of the mitochondrial membranes", *Trends Biochem Sci* (Feb. 1996) 21(2):51-2.
Segui-Real, B. et al., "Functional independence of the protein translocation machineries in mitochondrial outer and inner membranes: passage of preproteins through the intermembrane space", *The EMBO Journal*, 12(5):2211-2218 (1993).
Pačes, Václav et al., "The β subunit of the mitochondrial processing peptidase from rat liver: Cloning and sequencing of a cDNA and comparison with a proposed family of metallopeptidases", *Proc. Natl. Acad. Sci. USA*, vol. 90, pp. 5355-5358, Jun. 1993.
Beal, M.F., "Mitochondrial dysfunction in neurodegenerative diseases", *Biochem. Biophys. Acta* 1366 (1998) pp. 211-223.
DiMauro, Salvatore et al., "Mitochondria and heart disease", *Current Opinion in Cardiology*, 13(3):190-7 (1998).

(Continued)

*Primary Examiner*—Rebecca E. Prouty
*Assistant Examiner*—Delia M. Ramirez
(74) *Attorney, Agent, or Firm*—Foley & Lardner LLP

(57) ABSTRACT

The invention provides human mitochondrial proteins (MITP) and polynucleotides which identify and encode MITP. The invention also provides expression vectors, host cells, antibodies, agonists, and antagonists. The invention also provides methods for diagnosing, treating, or preventing disorders associated with expression of MITP.

5 Claims, No Drawings

OTHER PUBLICATIONS

Susin, S.A. et al., "Mitochondria as regulators of apoptosis: doubt no more", *Biochim. Biophys. Acta,* 1366 (1998) pp. 151-165.

Arizmendi, J.M. et al., "NADH:ubiquinone oxidoreductase from bovine heart mitochondria, A fourth nuclear encoded subunit with a homologue encoded in chloroplast genomes", *FEBS Letters,* vol. 301, n. 3, pp. 237-242 (Apr. 1992).

Braun, H. et al., "Primary structure, cell-free synthesis and mitochondrial targeting of the 8.2 kDa protein of cytochrome c reductase from potato", *Biochim Biophys Acta,* 1188(3):367-372 (Dec. 30, 1994).

Arizmendi, J.M. et al., GenBank Sequence Database (Accession X65020), National Center for Biotechnology Information, National Library of Medicine, Bethesda, Maryland 20894 (GI 11256); Nov. 29, 1994.

Zhang, Q. et al., GenBank Sequence Database (Accession AF085361), National Center for Biotechnology Information, National Library of Medicine, Bethesda, Maryland 20894 (GI 5114056); Jun. 22, 1999.

Jang, J.S. et al., GenBank Sequence Database (Accession AF176008), National Center for Biotechnology Information, National Library of Medicine, Bethesda, Maryland 20894 (GI 5815344); Sep. 15, 1999.

Wilks, J. et al., GenBank Sequence Database (Accession U31629), National Center for Biotechnology Information, National Library of Medicine, Bethesda, Maryland 20894 (GI 1172104); Jan. 31, 1996.

Stoneking, T. et al., GenBank Sequence Database (Accession AF104919), National Center for Biotechnology Information, National Library of Medicine, Bethesda, Maryland 20894 (GI 3859590); Nov. 11, 1998.

Wild, A., GenBank Sequence Database (Accession AL021366), National Center for Biotechnology Information, National Library of Medicine, Bethesda, Maryland 20894 (GI 3169115); Nov. 23, 1999.

Luo, W.Q. et al., GenBank Sequence Database (Accession AF106943), National Center for Biotechnology Information, National Library of Medicine, Bethesda, Maryland 20894 (GI 4454994); Mar. 21, 1999.

Blattner, F.R. et al., GenBank Sequence Database (Accession AE000486), National Center for Biotechnology Information, National Library of Medicine, Bethesda, Maryland 20894 (GI 1790574); Nov. 12, 1998.

Seki, N. et al., GenBank Sequence Database (Accession AB007915), National Center for Biotechnology Information, National Library of Medicine, Bethesda, Maryland 20894 (GI 6634034); Dec. 23, 1999.

Cummings, P.N., GenBank Sequence Database (Accession Z70310), National Center for Biotechnology Information, National Library of Medicine, Bethesda, Maryland 20894 (GI 1246478); Dec. 14, 1999.

Wilson, R. et al., GenBank Sequence Database (Accession U21324), National Center for Biotechnology Information, National Library of Medicine, Bethesda, Maryland 20894 (GI 687879); Mar. 2, 1995.

Lee, M.-C. et al., GenBank Sequence Database (Accession U86018), National Center for Biotechnology Information, National Library of Medicine, Bethesda, Maryland 20894 (GI 1835730); Feb. 10, 1997.

Braun, H., GenBank Sequence Database (Accession X79275), National Center for Biotechnology Information, National Library of Medicine, Bethesda, Maryland 20894 (GI 633686); Jul. 6, 1995.

* cited by examiner

ISOLATED POLYNUCLEOTIDE ENCODING A HUMAN PSST SUBUNIT OF THE NADH:UBIQUINONE OXIDOREDUCTASE COMPLEX

This application claims benefit of 60/124,655 filed on Mar. 16, 1999.

TECHNICAL FIELD

This invention relates to nucleic acid and amino acid sequences of mitochondrial proteins and to the use of these sequences in the diagnosis, treatment, and prevention of disorders of cell proliferation, inflammation, and immune response.

BACKGROUND OF THE INVENTION

Mitochondria are the primary sites of energy production in cells. Energy is produced by the oxidation of glucose and fatty acids. Glucose is initially oxidized to pyruvate in the cytoplasm. Fatty acids and pyruvate are transported to the mitochondria for complete oxidation to $CO_2$ by coenzyme A (CoA). This oxidation is coupled by enzymes to the transport of electrons from NADH and $FADH_2$ to oxygen and to the synthesis of ATP (oxidative phosphorylation) from ADP and $P_i$. ATP synthesis is carried out by the $F_0F_1$ ATPase complex in the mitochondrial inner membrane. ATP then provides the primary source of energy for driving a cell's many energy-requiring reactions.

Enzyme complexes responsible for electron transport and ATP synthesis include $F_0$, ubiquinone (CoQ)-cytochrome c reductase, cytochrome b, cytochrome $c_1$, FeS protein, and cytochrome c oxidase. ATP synthesis requires membrane transport enzymes including the phosphate transporter and the ATP-ADP antiport protein. The ATP-binding casette (ABC) superfamily of transport proteins is also observed in mitochondria (Hogue, D. L. et al. (1999) J. Mol. Biol. 285:379–389). Another mitochondrial transport enzyme is brown fat uncoupling protein, which dissipates oxidative energy as heat, and may be involved in the fever response to infection and trauma (Cannon, B. et al. (1998) Ann. NY Acad. Sci 856:171–187).

Electron carriers such as cytochromes accept electrons from NADH or $FADH_2$ and donate them to other electron carriers. Most electron-transferring proteins, except ubiquinone, are prosthetic groups such as flavins, heme, FeS clusters, and copper, bound to inner membrane proteins. Adrenodoxin, for example, is an FeS protein that forms a complex with NADPH:adrenodoxin reductase and cytochrome P450. Cytochromes contain a heme prosthetic group, a porphyrin ring containing a tightly bound iron atom. For a review of mitochondrial metabolism and regulation, see Lodish, H. et al. (1995) *Molecular Cell Biology*, Scientific American Books, New York N.Y., pp. 745–797.

The majority of mitochondrial proteins are encoded by nuclear genes, are synthesized on cytosolic ribosomes, and are imported into the mitochondria. Nuclear-encoded proteins which are destined for the mitochondrial matrix typically contain positively-charged amino terminal signal sequences. Import of these preproteins from the cytoplasm requires a multisubunit protein complex in the outer membrane known as the translocase of outer mitochondrial membrane (TOM; previously designated MOM; Pfanner, N. et al. (1996) Trends Biochem Sci. 21:51–52) and at least three inner membrane proteins which comprise the translocase of inner mitochondrial membrane (TIM; previously designated MIM; Pfanner et al., supra). An inside-negative membrane potential across the inner mitochondrial membrane is also required for preprotein import. Preproteins are recognized by surface receptor components of the TOM complex and are translocated through a proteinaceous pore formed by other TOM components. Proteins targeted to the matrix are then recognized by the import machinery of the TIM complex. The import systems of the outer and inner membranes can function independently (Segui-Real, B. et al. (1993) EMBO J. 12:2211–2218).

Once precursor proteins have entered the mitochondria, the leader peptide is cleaved by a signal peptidase to generate the mature protein. Most leader peptides are removed in a one step process by a protease termed mitochondrial processing peptidase (MPP) (Paces, V. et al. (1993) Proc. Natl. Acad. Sci. USA 90:5355–5358). In some cases a two-step process occurs in which MPP generates an intermediate precursor form which is cleaved by a second enzyme, mitochondrial intermediate peptidase, to generate the mature protein.

Mitochondrial dysfunction leads to impaired calcium buffering, generation of free radicals that may participate in deleterious intracellular and extracellular processes, changes in mitochondrial permeability, and oxidative damage which is observed in several neurodegenerative diseases. Neurodegenerative diseases linked to mitochondrial dysfunction include some forms of Alzheimer's disease, Friedreich's ataxia, familial amyotrophic lateral sclerosis, and Huntington's disease (Beal, M. F. (1998) Biochim. Biophys. Acta 1366:211–213). The myocardium is heavily dependent on oxidative metabolism, so mitochondrial dysfunction often leads to heart disease (DiMauro, S. and M. Hirano (1998) Curr. Opin. Cardiol. 13:190–197). Mitochondria are implicated in disorders of cell proliferation, since they play an important role in a cell's decision to proliferate or self-destruct through apoptosis. The oncoprotein Bcl-2, for example, promotes cell proliferation by stabilizing mitochondrial membranes so that apoptosis signals are not released (Susin, S. A. (1998) Biochim. Biophys. Acta 1366: 151–165).

The discovery of new mitochondrial proteins and the polynucleotides encoding them satisfies a need in the art by providing new compositions which are useful in the diagnosis, prevention, and treatment of disorders of cell proliferation, inflammation, and immune response.

SUMMARY OF THE INVENTION

The invention features purified polypeptides, mitochondrial proteins, referred to collectively as "MITP" and individually as "MITP-1," "MITP-2," "MITP-3," "MITP-4," "MITP-5," "MITP-6," "MITP-7," and "MITP-8." In one aspect, the invention provides an isolated polypeptide comprising a) an amino acid sequence selected from the group consisting of SEQ ID NO:1–8, b) a naturally occurring amino acid sequence having at least 90% sequence identity to an amino acid sequence selected from the group consisting of SEQ ID NO:1–8, c) a biologically active fragment of an amino acid sequence selected from the group consisting of SEQ ID NO:1–8, or d) an immunogenic fragment of an amino acid sequence selected from the group consisting of SEQ ID NO:1–8. In one alternative, the invention provides an isolated polypeptide comprising the amino acid sequence of SEQ ID NO:1–8.

The invention further provides an isolated polynucleotide encoding a polypeptide comprising a) an amino acid sequence selected from the group consisting of SEQ ID NO:1–8, b) a naturally occurring amino acid sequence having at least 90% sequence identity to an amino acid sequence selected from the group consisting of SEQ ID NO:1–8, c) a biologically active fragment of an amino acid sequence selected from the group consisting of SEQ ID NO:1–8, or d) an immunogenic fragment of an amino acid sequence selected from the group consisting of SEQ ID NO:1–8. In one alternative, the polynucleotide is selected from the group consisting of SEQ ID NO:9–16.

Additionally, the invention provides a recombinant polynucleotide comprising a promoter sequence operably linked to a polynucleotide encoding a polypeptide comprising a) an amino acid sequence selected from the group consisting of SEQ ID NO:1–8, b) a naturally occurring amino acid sequence having at least 90% sequence identity to an amino acid sequence selected from the group consisting of SEQ ID NO:1–8, c) a biologically active fragment of an amino acid sequence selected from the group consisting of SEQ ID NO:1–8, or d) an immunogenic fragment of an amino acid sequence selected from the group consisting of SEQ ID NO:1–8. In one alternative, the invention provides a cell transformed with the recombinant polynucleotide. In another alternative, the invention provides a transgenic organism comprising the recombinant polynucleotide.

The invention also provides a method for producing a polypeptide comprising a) an amino acid sequence selected from the group consisting of SEQ ID NO:1–8, b) a naturally occurring amino acid sequence having at least 90% sequence identity to an amino acid sequence selected from the group consisting of SEQ ID NO:1–8, c) a biologically active fragment of an amino acid sequence selected from the group consisting of SEQ ID NO:1–8, or d) an immunogenic fragment of an amino acid sequence selected from the group consisting of SEQ ID NO:1–8. The method comprises a) culturing a cell under conditions suitable for expression of the polypeptide, wherein said cell is transformed with a recombinant polynucleotide comprising a promoter sequence operably linked to a polynucleotide encoding the polypeptide, and b) recovering the polypeptide so expressed.

Additionally, the invention provides an isolated antibody which specifically binds to a polypeptide comprising a) an amino acid sequence selected from the group consisting of SEQ ID NO:1–8, b) a naturally occurring amino acid sequence having at least 90% sequence identity to an amino acid sequence selected from the group consisting of SEQ ID NO:1–8, c) a biologically active fragment of an amino acid sequence selected from the group consisting of SEQ ID NO:1–8, or d) an immunogenic fragment of an amino acid sequence selected from the group consisting of SEQ ID NO:1–8.

The invention further provides an isolated polynucleotide comprising a) a polynucleotide sequence selected from the group consisting of SEQ ID NO:9–16, b) a naturally occurring polynucleotide sequence having at least 70% sequence identity to a polynucleotide sequence selected from the group consisting of SEQ ID NO:9–16, c) a polynucleotide sequence complementary to a), or d) a polynucleotide sequence complementary to b). In one alternative, the polynucleotide comprises at least 60 contiguous nucleotides.

Additionally, the invention provides a method for detecting a target polynucleotide in a sample, said target polynucleotide having a sequence of a polynucleotide comprising a) a polynucleotide sequence selected from the group consisting of SEQ ID NO:9–16, b) a naturally occurring polynucleotide sequence having at least 70% sequence identity to a polynucleotide sequence selected from the group consisting of SEQ ID NO:9–16, c) a polynucleotide sequence complementary to a), or d) a polynucleotide sequence complementary to b). The method comprises a) hybridizing the sample with a probe comprising at least 16 contiguous nucleotides comprising a sequence complementary to said target polynucleotide in the sample, and which probe specifically hybridizes to said target polynucleotide, under conditions whereby a hybridization complex is formed between said probe and said target polynucleotide, and b) detecting the presence or absence of said hybridization complex, and optionally, if present, the amount thereof. In one alternative, the probe comprises at least 30 contiguous nucleotides. In another alternative, the probe comprises at least 60 contiguous nucleotides.

The invention further provides a pharmaceutical composition comprising an effective amount of a polypeptide comprising a) an amino acid sequence selected from the group consisting of SEQ ID NO:1–8, b) a naturally occurring amino acid sequence having at least 90% sequence identity to an amino acid sequence selected from the group consisting of SEQ ID NO:1–8, c) a biologically active fragment of an amino acid sequence selected from the group consisting of SEQ ID NO:1–8, or d) an immunogenic fragment of an amino acid sequence selected from the group consisting of SEQ ID NO:1–8, and a pharmaceutically acceptable excipient. The invention additionally provides a method of treating a disease or condition associated with decreased expression of functional MITP, comprising administering to a patient in need of such treatment the pharmaceutical composition.

The invention also provides a method for screening a compound for effectiveness as an agonist of a polypeptide comprising a) an amino acid sequence selected from the group consisting of SEQ ID NO:1–8, b) a naturally occurring amino acid sequence having at least 90% sequence identity to an amino acid sequence selected from the group consisting of SEQ ID NO:1–8, c) a biologically active fragment of an amino acid sequence selected from the group consisting of SEQ ID NO:1–8, or d) an immunogenic fragment of an amino acid sequence selected from the group consisting of SEQ ID NO:1–8. The method comprises a) exposing a sample comprising the polypeptide to a compound, and b) detecting agonist activity in the sample. In one alternative, the invention provides a pharmaceutical composition comprising an agonist compound identified by the method and a pharmaceutically acceptable excipient. In another alternative, the invention provides a method of treating a disease or condition associated with decreased expression of functional MITP, comprising administering to a patient in need of such treatment the pharmaceutical composition.

Additionally, the invention provides a method for screening a compound for effectiveness as an antagonist of a polypeptide comprising a) an amino acid sequence selected from the group consisting of SEQ ID NO:1–8, b) a naturally occurring amino acid sequence having at least 90% sequence identity to an amino acid sequence selected from the group consisting of SEQ ID NO:1–8, c) a biologically active fragment of an amino acid sequence selected from the group consisting of SEQ ID NO:1–8, or d) an immunogenic fragment of an amino acid sequence selected from the group consisting of SEQ ID NO:1–8. The method comprises a) exposing a sample comprising the polypeptide to a compound, and b) detecting antagonist activity in the sample. In one alternative, the invention provides a pharmaceutical composition comprising an antagonist compound identified by the method and a pharmaceutically acceptable excipient. In another alternative, the invention provides a method of treating a disease or condition associated with overexpression of functional MITP, comprising administering to a patient in need of such treatment the pharmaceutical composition.

The invention further provides a method for screening a compound for effectiveness in altering expression of a target polynucleotide, wherein said target polynucleotide comprises a sequence selected from the group consisting of SEQ ID NO:9–16, the method comprising a) exposing a sample comprising the target polynucleotide to a compound, and b) detecting altered expression of the target polynucleotide.

BRIEF DESCRIPTION OF THE TABLES

Table 1 shows polypeptide and nucleotide sequence identification numbers (SEQ ID NOs), clone identification numbers (clone IDs), cDNA libraries, and cDNA fragments used to assemble full-length sequences encoding MITP.

Table 2 shows features of each polypeptide sequence, including potential motifs, homologous sequences, and methods, algorithms, and searchable databases used for analysis of MITP.

Table 3 shows the tissue-specific expression patterns of each nucleic acid sequence as determined by northern analysis; diseases, disorders, or conditions associated with these tissues; and the vector into which each cDNA was cloned.

Table 4 describes the tissues used to construct the cDNA libraries from which cDNA clones encoding MITP were isolated.

Table 5 shows the tools, programs, and algorithms used to analyze MITP, along with applicable descriptions, references, and threshold parameters.

DESCRIPTION OF THE INVENTION

Before the present proteins, nucleotide sequences, and methods are described, it is understood that this invention is not limited to the particular machines, materials and methods described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a," "an," and "the" include plural reference unless the context clearly dictates otherwise. Thus, for example, a reference to "a host cell" includes a plurality of such host cells, and a reference to "an antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any machines, materials, and methods similar or equivalent to those described herein can be used to practice or test the present invention, the preferred machines, materials and methods are now described. All publications mentioned herein are cited for the purpose of describing and disclosing the cell lines, protocols, reagents and vectors which are reported in the publications and which might be used in connection with the invention. Nothing herein is to be construed as an admission that the invention is not entitled to antedate such disclosure by virtue of prior invention.

Definitions

"MITP" refers to the amino acid sequences of substantially purified MITP obtained from any species, particularly a mammalian species, including bovine, ovine, porcine, murine, equine, and human, and from any source, whether natural, synthetic, semi-synthetic, or recombinant.

The term "agonist" refers to a molecule which intensifies or mimics the biological activity of MITP. Agonists may include proteins, nucleic acids, carbohydrates, small molecules, or any other compound or composition which modulates the activity of MITP either by directly interacting with MITP or by acting on components of the biological pathway in which MITP participates.

An "allelic variant" is an alternative form of the gene encoding MITP. Allelic variants may result from at least one mutation in the nucleic acid sequence and may result in altered mRNAs or in polypeptides whose structure or function may or may not be altered. A gene may have none, one, or many allelic variants of its naturally occurring form. Common mutational changes which give rise to allelic variants are generally ascribed to natural deletions, additions, or substitutions of nucleotides. Each of these types of changes may occur alone, or in combination with the others, one or more times in a given sequence.

"Altered" nucleic acid sequences encoding MITP include those sequences with deletions, insertions, or substitutions of different nucleotides, resulting in a polypeptide the same as MITP or a polypeptide with at least one functional characteristic of MITP. Included within this definition are polymorphisms which may or may not be readily detectable using a particular oligonucleotide probe of the polynucleotide encoding MITP, and improper or unexpected hybridization to allelic variants, with a locus other than the normal chromosomal locus for the polynucleotide sequence encoding MITP. The encoded protein may also be "altered," and may contain deletions, insertions, or substitutions of amino acid residues which produce a silent change and result in a functionally equivalent MITP. Deliberate amino acid substitutions may be made on the basis of similarity in polarity, charge, solubility, hydrophobicity, hydrophilicity, and/or the amphipathic nature of the residues, as long as the biological or immunological activity of MITP is retained. For example, negatively charged amino acids may include aspartic acid and glutamic acid, and positively charged amino acids may include lysine and arginine. Amino acids with uncharged polar side chains having similar hydrophilicity values may include: asparagine and glutamine; and serine and threonine. Amino acids with uncharged side chains having similar hydrophilicity values may include: leucine, isoleucine, and valine; glycine and alanine; and phenylalanine and tyrosine.

The terms "amino acid" and "amino acid sequence" refer to an oligopeptide, peptide, polypeptide, or protein sequence, or a fragment of any of these, and to naturally occurring or synthetic molecules. Where "amino acid sequence" is recited to refer to an amino acid sequence of a naturally occurring protein molecule, "amino acid sequence" and like terms are not meant to limit the amino acid sequence to the complete native amino acid sequence associated with the recited protein molecule.

"Amplification" relates to the production of additional copies of a nucleic acid sequence. Amplification is generally carried out using polymerase chain reaction (PCR) technologies well known in the art.

The term "antagonist" refers to a molecule which inhibits or attenuates the biological activity of MITP. Antagonists may include proteins such as antibodies, nucleic acids, carbohydrates, small molecules, or any other compound or composition which modulates the activity of MITP either by directly interacting with MITP or by acting on components of the biological pathway in which MITP participates.

The term "antibody" refers to intact immunoglobulin molecules as well as to fragments thereof, such as Fab, F(ab')$_2$, and Fv fragments, which are capable of binding an epitopic determinant. Antibodies that bind MITP polypeptides can be prepared using intact polypeptides or using fragments containing small peptides of interest as the immunizing antigen. The polypeptide or oligopeptide used to immunize an animal (e.g., a mouse, a rat, or a rabbit) can be derived from the translation of RNA, or synthesized chemically, and can be conjugated to a carrier protein if desired. Commonly used carriers that are chemically coupled to peptides include bovine serum albumin, thyroglobulin, and keyhole limpet hemocyanin (KLH). The coupled peptide is then used to immunize the animal.

The term "antigenic determinant" refers to that region of a molecule (i.e., an epitope) that makes contact with a particular antibody. When a protein or a fragment of a protein is used to immunize a host animal, numerous regions of the protein may induce the production of antibodies which bind specifically to antigenic determinants (particular regions or three-dimensional structures on the protein). An antigenic determinant may compete with the intact antigen (i.e., the immunogen used to elicit the immune response) for binding to an antibody.

The term "antisense" refers to any composition capable of base-pairing with the "sense" strand of a specific nucleic acid sequence. Antisense compositions may include DNA; RNA; peptide nucleic acid (PNA); oligonucleotides having modified backbone linkages such as phosphorothioates, methylphosphonates, or benzylphosphonates; oligonucleotides having modified sugar groups such as 2'-methoxyethyl sugars or 2'-methoxyethoxy sugars; or oligonucleotides having modified bases such as 5-methyl cytosine, 2'-deoxyuracil, or 7-deaza-2'-deoxyguanosine. Antisense molecules may be produced by any method including chemical synthesis or transcription. Once introduced into a cell, the complementary antisense molecule base-pairs with a naturally occurring nucleic acid sequence produced by the cell to form duplexes which block either transcription or translation. The designation "negative" or "minus" can refer to the antisense strand, and the designation "positive" or "plus" can refer to the sense strand of a reference DNA molecule.

The term "biologically active" refers to a protein having structural, regulatory, or biochemical functions of a naturally occurring molecule. Likewise, "immunologically active" refers to the capability of the natural, recombinant, or synthetic MITP, or of any oligopeptide thereof, to induce a specific immune response in appropriate animals or cells and to bind with specific antibodies.

The terms "complementary" and "complementarity" refer to the natural binding of polynucleotides by base pairing. For example, the sequence "5' A-G-T 3'" bonds to the complementary sequence "3' T-C-A 5'." Complementarity between two single-stranded molecules may be "partial," such that only some of the nucleic acids bind, or it may be "complete," such that total complementarity exists between the single stranded molecules. The degree of complementarity between nucleic acid strands has significant effects on the efficiency and strength of the hybridization between the nucleic acid strands. This is of particular importance in amplification reactions, which depend upon binding between nucleic acid strands, and in the design and use of peptide nucleic acid (PNA) molecules.

A "composition comprising a given polynucleotide sequence" and a "composition comprising a given amino acid sequence" refer broadly to any composition containing the given polynucleotide or amino acid sequence. The composition may comprise a dry formulation or an aqueous solution. Compositions comprising polynucleotide sequences encoding MITP or fragments of MITP may be employed as hybridization probes. The probes may be stored in freeze-dried form and may be associated with a stabilizing agent such as a carbohydrate. In hybridizations, the probe may be deployed in an aqueous solution containing salts (e.g., NaCl), detergents (e.g., sodium dodecyl sulfate; SDS), and other components (e.g., Denhardt's solution, dry milk, salmon sperm DNA, etc.).

"Consensus sequence" refers to a nucleic acid sequence which has been resequenced to resolve uncalled bases, extended using the XL-PCR kit (Perkin-Elmer, Norwalk Conn.) in the 5' and/or the 3' direction, and resequenced, or which has been assembled from the overlapping sequences of one or more Incyte Clones and, in some cases, one or more public domain ESTs, using a computer program for fragment assembly, such as the GELVIEW fragment assembly system (GCG, Madison Wis.). Some sequences have been both extended and assembled to produce the consensus sequence.

"Conservative amino acid substitutions" are those substitutions that, when made, least interfere with the properties of the original protein, i.e., the structure and especially the function of the protein is conserved and not significantly changed by such substitutions. The table below shows amino acids which may be substituted for an original amino acid in a protein and which are regarded as conservative amino acid substitutions.

| Original Residue | Conservative Substitution |
| --- | --- |
| Ala | Gly, Ser |
| Arg | His, Lys |
| Asn | Asp, Gln, His |
| Asp | Asn, Glu |
| Cys | Ala, Ser |
| Gln | Asn, Glu, His |
| Glu | Asp, Gln, His |
| Gly | Ala |
| His | Asn, Arg, Gln, Glu |
| Ile | Leu, Val |
| Leu | Ile, Val |
| Lys | Arg, Gln, Glu |
| Met | Leu, Ile |
| Phe | His, Met, Leu, Trp, Tyr |
| Ser | Cys, Thr |
| Thr | Ser, Val |
| Trp | Phe, Tyr |
| Tyr | His, Phe, Trp |
| Val | Ile, Leu, Thr |

Conservative amino acid substitutions generally maintain (a) the structure of the polypeptide backbone in the area of the substitution, for example, as a beta sheet or alpha helical conformation, (b) the charge or hydrophobicity of the molecule at the site of the substitution, and/or (c) the bulk of the side chain.

A "deletion" refers to a change in the amino acid or nucleotide sequence that results in the absence of one or more amino acid residues or nucleotides.

The term "derivative" refers to the chemical modification of a polypeptide sequence, or a polynucleotide sequence. Chemical modifications of a polynucleotide sequence can include, for example, replacement of hydrogen by an alkyl, acyl, hydroxyl, or amino group. A derivative polynucleotide encodes a polypeptide which retains at least one biological or immunological function of the natural molecule. A derivative polypeptide is one modified by glycosylation, pegylation, or any similar process that retains at least one biological or immunological function of the polypeptide from which it was derived.

A "fragment" is a unique portion of MITP or the polynucleotide encoding MITP which is identical in sequence to but shorter in length than the parent sequence. A fragment may comprise up to the entire length of the defined sequence, minus one nucleotide/amino acid residue. For example, a fragment may comprise from 5 to 1000 contiguous nucleotides or amino acid residues. A fragment used as a probe, primer, antigen, therapeutic molecule, or for other purposes, may be at least 5, 10, 15, 20, 25, 30, 40, 50, 60, 75, 100, 150, 250 or at least 500 contiguous nucleotides or amino acid residues in length. Fragments may be preferentially selected from certain regions of a molecule. For example, a polypeptide fragment may comprise a certain length of contiguous amino acids selected from the first 250 or 500 amino acids (or first 25% or 50% of a polypeptide) as shown in a certain defined sequence. Clearly these lengths are exemplary, and any length that is supported by the specification, including the Sequence Listing, tables, and figures, may be encompassed by the present embodiments.

A fragment of SEQ ID NO:9–16 comprises a region of unique polynucleotide sequence that specifically identifies SEQ ID NO:9–16, for example, as distinct from any other sequence in the same genome. A fragment of SEQ ID NO:9–16 is useful, for example, in hybridization and amplification technologies and in analogous methods that distinguish SEQ ID NO:9–16 from related polynucleotide sequences. The precise length of a fragment of SEQ ID NO:9–16 and the region of SEQ ID NO:9–16 to which the fragment corresponds are routinely determinable by one of ordinary skill in the art based on the intended purpose for the fragment.

A fragment of SEQ ID NO: 1–8 is encoded by a fragment of SEQ ID NO:9–16. A fragment of SEQ ID NO:1–8 comprises a region of unique amino acid sequence that specifically identifies SEQ ID NO:1–8. For example, a fragment of SEQ ID NO:1–8 is useful as an immunogenic peptide for the development of antibodies that specifically recognize SEQ ID NO:1–8. The precise length of a fragment of SEQ ID NO:1–8 and the region of SEQ ID NO:1–8 to which the fragment corresponds are routinely determinable by one of ordinary skill in the art based on the intended purpose for the fragment.

The term "similarity" refers to a degree of complementarity. There may be partial similarity or complete similarity. The word "identity" may substitute for the word "similarity." A partially complementary sequence that at least partially inhibits an identical sequence from hybridizing to a target nucleic acid is referred to as "substantially similar." The inhibition of hybridization of the completely complementary sequence to the target sequence may be examined using a hybridization assay (Southern or northern blot, solution hybridization, and the like) under conditions of reduced stringency. A substantially similar sequence or hybridization probe will compete for and inhibit the binding of a completely similar (identical) sequence to the target sequence under conditions of reduced stringency. This is not to say that conditions of reduced stringency are such that non-specific binding is permitted, as reduced stringency conditions require that the binding of two sequences to one another be a specific (i.e., a selective) interaction. The absence of non-specific binding may be tested by the use of a second target sequence which lacks even a partial degree of complementarity (e.g., less than about 30% similarity or identity). In the absence of non-specific binding, the substantially similar sequence or probe will not hybridize to the second non-complementary target sequence.

The phrases "percent identity" and "% identity," as applied to polynucleotide sequences, refer to the percentage of residue matches between at least two polynucleotide sequences aligned using a standardized algorithm. Such an algorithm may insert, in a standardized and reproducible way, gaps in the sequences being compared in order to optimize alignment between two sequences, and therefore achieve a more meaningful comparison of the two sequences.

Percent identity between polynucleotide sequences may be determined using the default parameters of the CLUSTAL V algorithm as incorporated into the MEGALIGN version 3.12e sequence alignment program. This program is part of the LASERGENE software package, a suite of molecular biological analysis programs (DNASTAR, Madison Wis.). CLUSTAL V is described in Higgins, D. G. and P. M. Sharp (1989) CABIOS 5:151–153 and in Higgins, D. G. et al. (1992) CABIOS 8:189–191. For pairwise alignments of polynucleotide sequences, the default parameters are set as follows: Ktuple=2, gap penalty=5, window=4, and "diagonals saved"=4. The "weighted" residue weight table is selected as the default. Percent identity is reported by CLUSTAL V as the "percent similarity" between aligned polynucleotide sequence pairs.

Alternatively, a suite of commonly used and freely available sequence comparison algorithms is provided by the National Center for Biotechnology Information (NCBI) Basic Local Alignment Search Tool (BLAST) (Altschul, S. F. et al. (1990) J. Mol. Biol. 215:403410), which is available from several sources, including the NCBI, Bethesda, Md., and on the Internet at http://www.ncbinih.gov/BLAST/. The BLAST software suite includes various sequence analysis programs including "blastn," that is used to align a known polynucleotide sequence with other polynucleotide sequences from a variety of databases. Also available is a tool called "BLAST 2 Sequences" that is used for direct pairwise comparison of two nucleotide sequences. "BLAST 2 Sequences" can be accessed and used interactively at http://www.ncbi.nlm.nih.gov/gorf/b12.html. The "BLAST 2 Sequences" tool can be used for both blastn and blastp (discussed below). BLAST programs are commonly used with gap and other parameters set to default settings. For example, to compare two nucleotide sequences, one may use blastn with the "BLAST 2 Sequences" tool Version 2.0.9 (May-07-1999) set at default parameters. Such default parameters may be, for example:

Matrix: BLOSUM62
Reward for match: 1
Penalty for mismatch: −2
Open Gap: 5 and Extension Gap: 2 penalties
Gap×drop-off: 50
Expect: 10
Word Size: 11
Filter: on Percent identity may be measured over the length of an entire defined sequence, for example, as defined by a particular SEQ ID number, or may be measured over a shorter length, for example, over the length of a fragment taken from a larger, defined sequence, for instance, a fragment of at least 20, at least 30, at least 40, at least 50, at least 70, at least 100, or at least 200 contiguous nucleotides. Such lengths are exemplary only, and it is understood that any fragment length supported by the sequences shown herein, in the tables, figures, or Sequence Listing, may be used to describe a length over which percentage identity may be measured.

Nucleic acid sequences that do not show a high degree of identity may nevertheless encode similar amino acid sequences due to the degeneracy of the genetic code. It is understood that changes in a nucleic acid sequence can be made using this degeneracy to produce multiple nucleic acid sequences that all encode substantially the same protein.

The phrases "percent identity" and "% identity," as applied to polypeptide sequences, refer to the percentage of residue matches between at least two polypeptide sequences aligned using a standardized algorithm Methods of polypeptide sequence alignment are well-known. Some alignment methods take into account conservative amino acid substitutions. Such conservative substitutions, explained in more detail above, generally preserve the hydrophobicity and acidity at the site of substitution, thus preserving the structure (and therefore function) of the polypeptide.

Percent identity between polypeptide sequences may be determined using the default parameters of the CLUSTAL V algorithm as incorporated into the MEGALIGN version 3.12e sequence alignment program (described and referenced above). For pairwise alignments of polypeptide sequences using CLUSTAL V, the default parameters are set as follows: Ktuple=1, gap penalty=3, window=5, and "diagonals saved"=5. The PAM250 matrix is selected as the default residue weight table. As with polynucleotide alignments, the percent identity is reported by CLUSTAL V as the "percent similarity" between aligned polypeptide sequence pairs.

Alternatively the NCBI BLAST software suite may be used. For example, for a pairwise comparison of two polypeptide sequences, one may use the "BLAST 2 Sequences" tool Version 2.0.9 (May-07-1999) with blastp set at default parameters. Such default parameters may be, for example:

Matrix: BLOSUM62
Open Gap: 11 and Extension Gap: 1 penalties
Gap×drop-off: 50
Expect: 10
Word Size: 3
Filter: on Percent identity may be measured over the length of an entire defined polypeptide sequence, for example, as defined by a particular SEQ ID number, or may be measured over a shorter length, for example, over the length of a fragment taken from a larger, defined polypeptide sequence, for instance, a fragment of at least 15, at least 20, at least 30, at least 40, at least 50, at least 70 or at least 150 contiguous residues. Such lengths are exemplary only, and it is understood that any fragment length supported by the sequences shown herein, in the tables, figures or Sequence Listing, may be used to describe a length over which percentage identity may be measured.

"Human artificial chromosomes" (HACs) are linear microchromosomes which may contain DNA sequences of about 6 kb to 10 Mb in size, and which contain all of the elements required for stable mitotic chromosome segregation and maintenance.

The term "humanized antibody" refers to antibody molecules in which the amino acid sequence in the non-antigen binding regions has been altered so that the antibody more closely resembles a human antibody, and still retains its original binding ability.

"Hybridization" refers to the process by which a polynucleotide strand anneals with a complementary strand through base pairing under defined hybridization conditions. Specific hybridization is an indication that two nucleic acid sequences share a high degree of identity. Specific hybridization complexes form under permissive annealing conditions and remain hybridized after the "washing" step(s). The washing step(s) is particularly important in determining the stringency of the hybridization process, with more stringent conditions allowing less non-specific binding, i.e., binding between pairs of nucleic acid strands that are not perfectly matched. Permissive conditions for annealing of nucleic acid sequences are routinely determinable by one of ordinary skill in the art and may be consistent among hybridization experiments, whereas wash conditions may be varied among experiments to achieve the desired stringency, and therefore hybridization specificity. Permissive annealing conditions occur, for example, at 68° C. in the presence of about 6×SSC, about 1% (w/v) SDS, and about 100 μg/ml denatured salmon sperm DNA.

Generally, stringency of hybridization is expressed, in part, with reference to the temperature under which the wash step is carried out. Generally, such wash temperatures are selected to be about 5° C. to 20° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. An equation for calculating $T_m$ and conditions for nucleic acid hybridization are well known and can be found in Sambrook et al., 1989, *Molecular Cloning: A Laboratory Manual, 2$^{nd}$ ed.*, vol. 1–3, Cold Spring Harbor Press, Plainview N.Y.; specifically see volume 2, chapter 9.

High stringency conditions for hybridization between polynucleotides of the present invention include wash conditions of 68° C. in the presence of about 0.2×SSC and about 0.1% SDS, for 1 hour. Alternatively, temperatures of about 65° C., 60° C., 55° C., or 42° C. may be used. SSC concentration may be varied from about 0.1 to 2× SSC, with SDS being present at about 0.1%. Typically, blocking reagents are used to block non-specific hybridization. Such blocking reagents include, for instance, denatured salmon sperm DNA at about 100–200 μg/ml. Organic solvent, such as formamide at a concentration of about 35–50% v/v, may also be used under particular circumstances, such as for RNA:DNA hybridizations. Useful variations on these wash conditions will be readily apparent to those of ordinary skill in the art. Hybridization, particularly under high stringency conditions, may be suggestive of evolutionary similarity between the nucleotides. Such similarity is strongly indicative of a similar role for the nucleotides and their encoded polypeptides.

The term "hybridization complex" refers to a complex formed between two nucleic acid sequences by virtue of the formation of hydrogen bonds between complementary bases. A hybridization complex may be formed in solution (e.g., $C_0t$ or $R_0t$ analysis) or formed between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

The words "insertion" and "addition" refer to changes in an amino acid or nucleotide sequence resulting in the addition of one or more amino acid residues or nucleotides, respectively.

"Immune response" can refer to conditions associated with inflammation, trauma, immune disorders, or infectious or genetic disease, etc. These conditions can be characterized by expression of various factors, e.g., cytokines, chemokines, and other signaling molecules, which may affect cellular and systemic defense systems.

An "immunogenic fragment" is a polypeptide or oligopeptide fragment of MITP which is capable of eliciting an immune response when introduced into a living organism, for example, a mammal. The term "immunogenic fragment" also includes any polypeptide or oligopeptide fragment of MITP which is useful in any of the antibody production methods disclosed herein or known in the art.

The term "microarray" refers to an arrangement of distinct polynucleotides on a substrate.

The terms "element" and "array element" in a microarray context, refer to hybridizable polynucleotides arranged on the surface of a substrate.

The term "modulate" refers to a change in the activity of MITP. For example, modulation may cause an increase or a decrease in protein activity, binding characteristics, or any other biological, functional, or immunological properties of MITP.

The phrases "nucleic acid" and "nucleic acid sequence" refer to a nucleotide, oligonucleotide, polynucleotide, or any fragment thereof. These phrases also refer to DNA or RNA of genomic or synthetic origin which may be single-stranded or double-stranded and may represent the sense or the antisense strand, to peptide nucleic acid (PNA), or to any DNA-like or RNA-like material.

"Operably linked" refers to the situation in which a first nucleic acid sequence is placed in a functional relationship with the second nucleic acid sequence. For instance, a promoter is operably linked to a coding sequence if the promoter affects the transcription or expression of the coding sequence. Generally, operably linked DNA sequences may be in close proximity or contiguous and, where necessary to join two protein coding regions, in the same reading frame.

"Peptide nucleic acid" (PNA) refers to an antisense molecule or anti-gene agent which comprises an oligonucleotide of at least about 5 nucleotides in length linked to a peptide backbone of amino acid residues ending in lysine. The terminal lysine confers solubility to the composition. PNAs preferentially bind complementary single stranded DNA or RNA and stop transcript elongation, and may be pegylated to extend their lifespan in the cell.

"Probe" refers to nucleic acid sequences encoding MITP, their complements, or fragments thereof, which are used to detect identical, allelic or related nucleic acid sequences. Probes are isolated oligonucleotides or polynucleotides attached to a detectable label or reporter molecule. Typical labels include radioactive isotopes, ligands, chemiluminescent agents, and enzymes. "Primers" are short nucleic acids, usually DNA oligonucleotides, which may be annealed to a target polynucleotide by complementary base-pairing. The primer may then be extended along the target DNA strand by a DNA polymerase enzyme. Primer pairs can be used for amplification (and identification) of a nucleic acid sequence, e.g., by the polymerase chain reaction (PCR).

Probes and primers as used in the present invention typically comprise at least 15 contiguous nucleotides of a known sequence. In order to enhance specificity, longer probes and primers may also be employed, such as probes and primers that comprise at least 20, 25, 30, 40, 50, 60, 70, 80, 90, 100, or at least 150 consecutive nucleotides of the disclosed nucleic acid sequences. Probes and primers may be considerably longer than these examples, and it is understood that any length supported by the specification, including the tables, figures, and Sequence Listing, may be used.

Methods for preparing and using probes and primers are described in the references, for example Sambrook et al., 1989, *Molecular Cloning: A Laboratory Manual*, $2^{nd}$ ed., vol. 1–3, Cold Spring Harbor Press, Plainview N.Y.; Ausubel et al., 1987, *Current Protocols in Molecular Biology*, Greene Publ. Assoc. & Wiley-Intersciences, New York N.Y.; Innis et al., 1990, *PCR Protocols, A Guide to Methods and Applications*, Academic Press, San Diego Calif. PCR primer pairs can be derived from a known sequence, for example, by using computer programs intended for that purpose such as Primer (Version 0.5, 1991, Whitehead Institute for Biomedical Research, Cambridge Mass.).

Oligonucleotides for use as primers are selected using software known in the art for such purpose. For example, OLIGO 4.06 software is useful for the selection of PCR primer pairs of up to 100 nucleotides each, and for the analysis of oligonucleotides and larger polynucleotides of up to 5,000 nucleotides from an input polynucleotide sequence of up to 32 kilobases. Similar primer selection programs have incorporated additional features for expanded capabilities. For example, the PrimOU primer selection program (available to the public from the Genome Center at University of Texas South West Medical Center, Dallas Tex.) is capable of choosing specific primers from megabase sequences and is thus useful for designing primers on a genome-wide scope. The Primer3 primer selection program (available to the public from the Whitehead Institute/MIT Center for Genome Research, Cambridge Mass.) allows the user to input a "mispriming library," in which sequences to avoid as primer binding sites are user-specified. Primer3 is useful, in particular, for the selection of oligonucleotides for microarrays. (The source code for the latter two primer selection programs may also be obtained from their respective sources and modified to meet the user's specific needs.) The PrimeGen program (available to the public from the UK Human Genome Mapping Project Resource Centre, Cambridge UK) designs primers based on multiple sequence alignments, thereby allowing selection of primers that hybridize to either the most conserved or least conserved regions of aligned nucleic acid sequences. Hence, this program is useful for identification of both unique and conserved oligonucleotides and polynucleotide fragments. The oligonucleotides and polynucleotide fragments identified by any of the above selection methods are useful in hybridization technologies, for example, as PCR or sequencing primers, microarray elements, or specific probes to identify fully or partially complementary polynucleotides in a sample of nucleic acids. Methods of oligonucleotide selection are not limited to those described above.

A "recombinant nucleic acid" is a sequence that is not naturally occurring or has a sequence that is made by an artificial combination of two or more otherwise separated segments of sequence. This artificial combination is often accomplished by chemical synthesis or, more commonly, by the artificial manipulation of isolated segments of nucleic acids, e.g., by genetic engineering techniques such as those described in Sambrook, supra. The term recombinant includes nucleic acids that have been altered solely by addition, substitution, or deletion of a portion of the nucleic acid. Frequently, a recombinant nucleic acid may include a nucleic acid sequence operably linked to a promoter sequence. Such a recombinant nucleic acid may be part of a vector that is used, for example, to transform a cell.

Alternatively, such recombinant nucleic acids may be part of a viral vector, e.g., based on a vaccinia virus, that could be use to vaccinate a mammal wherein the recombinant nucleic acid is expressed, inducing a protective immunological response in the mammal.

An "RNA equivalent," in reference to a DNA sequence, is composed of the same linear sequence of nucleotides as the reference DNA sequence with the exception that all occurrences of the nitrogenous base thymine are replaced with uracil, and the sugar backbone is composed of ribose instead of deoxyribose.

The term "sample" is used in its broadest sense. A sample suspected of containing nucleic acids encoding MITP, or fragments thereof, or MITP itself, may comprise a bodily fluid; an extract from a cell, chromosome, organelle, or membrane isolated from a cell; a cell; genomic DNA, RNA, or cDNA, in solution or bound to a substrate; a tissue; a tissue print; etc.

The terms "specific binding" and "specifically binding" refer to that interaction between a protein or peptide and an agonist, an antibody, an antagonist, a small molecule, or any natural or synthetic binding composition. The interaction is dependent upon the presence of a particular structure of the protein, e.g., the antigenic determinant or epitope, recognized by the binding molecule. For example, if an antibody is specific for epitope "A," the presence of a polypeptide containing the epitope A, or the presence of free unlabeled A, in a reaction containing free labeled A and the antibody will reduce the amount of labeled A that binds to the antibody.

The term "substantially purified" refers to nucleic acid or amino acid sequences that are removed from their natural environment and are isolated or separated, and are at least 60% free, preferably at least 75% free, and most preferably at least 90% free from other components with which they are naturally associated.

A "substitution" refers to the replacement of one or more amino acids or nucleotides by different amino acids or nucleotides, respectively.

"Substrate" refers to any suitable rigid or semi-rigid support including membranes, filters, chips, slides, wafers, fibers, magnetic or nonmagnetic beads, gels, tubing, plates, polymers, microparticles and capillaries. The substrate can have a variety of surface forms, such as wells, trenches, pins, channels and pores, to which polynucleotides or polypeptides are bound.

"Transformation" describes a process by which exogenous DNA enters and changes a recipient cell. Transformation may occur under natural or artificial conditions according to various methods well known in the art, and may rely on any known method for the insertion of foreign nucleic acid sequences into a prokaryotic or eukaryotic host cell. The method for transformation is selected based on the type of host cell being transformed and may include, but is not limited to, viral infection, electroporation, heat shock, lipofection, and particle bombardment. The term "transformed" cells includes stably transformed cells in which the inserted DNA is capable of replication either as an autonomously replicating plasmid or as part of the host chromosome, as well as transiently transformed cells which express the inserted DNA or RNA for limited periods of time.

A "transgenic organism," as used herein, is any organism, including but not limited to animals and plants, in which one or more of the cells of the organism contains heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. The transgenic organisms contemplated in accordance with the present invention include bacteria, cyanobacteria, fungi, and plants and animals. The isolated DNA of the present invention can be introduced into the host by methods known in the art, for example infection, transfection, transformation or transconjugation. Techniques for transferring the DNA of the present invention into such organisms are widely known and provided in references such as Sambrook et al. (1989), supra.

A "variant" of a particular nucleic acid sequence is defined as a nucleic acid sequence having at least 40% sequence identity to the particular nucleic acid sequence over a certain length of one of the nucleic acid sequences using blastn with the "BLAST 2 Sequences" tool Version 2.0.9 (May-07-1999) set at default parameters. Such a pair of nucleic acids may show, for example, at least 50%, at least 60%, at least 70%, at least 80%, at least 85%, at least 90%, at least 95% or at least 98% or greater sequence identity over a certain defined length. A variant may be described as, for example, an "allelic" (as defined above), "splice," "species," or "polymorphic" variant. A splice variant may have significant identity to a reference molecule, but will generally have a greater or lesser number of polynucleotides due to alternate splicing of exons during mRNA processing. The corresponding polypeptide may possess additional functional domains or lack domains that are present in the reference molecule. Species variants are polynucleotide sequences that vary from one species to another. The resulting polypeptides generally will have significant amino acid identity relative to each other. A polymorphic variant is a variation in the polynucleotide sequence of a particular gene between individuals of a given species. Polymorphic variants also may encompass "single nucleotide polymorphisms" (SNPs) in which the polynucleotide sequence varies by one nucleotide base. The presence of SNPs may be indicative of, for example, a certain population, a disease state, or a propensity for a disease state.

A "variant" of a particular polypeptide sequence is defined as a polypeptide sequence having at least 40% sequence identity to the particular polypeptide sequence over a certain length of one of the polypeptide sequences using blastp with the "BLAST 2 Sequences" tool Version 2.0.9 (May-07-1999) set at default parameters. Such a pair of polypeptides may show, for example, at least 50%, at least 60%, at least 70%, at least 80%, at least 90%, at least 95%, or at least 98% or greater sequence identity over a certain defined length of one of the polypeptides.

The Invention

The invention is based on the discovery of new human mitochondrial proteins (MITP), the polynucleotides encoding MITP, and the use of these compositions for the diagnosis, treatment, or prevention of disorders of cell proliferation, inflammation, and immune response.

Table 1 lists the Incyte clones used to assemble full length nucleotide sequences encoding MITP. Columns 1 and 2 show the sequence identification numbers (SEQ ID NOs) of the polypeptide and nucleotide sequences, respectively. Column 3 shows the clone IDs of the Incyte clones in which nucleic acids encoding each MITP were identified, and column 4 shows the cDNA libraries from which these clones were isolated. Column 5 shows Incyte clones and their corresponding cDNA libraries. Clones for which cDNA libraries are not indicated were derived from pooled cDNA libraries. The Incyte clones in column 5 were used to assemble the consensus nucleotide sequence of each MITP and are useful as fragments in hybridization technologies.

The columns of Table 2 show various properties of each of the polypeptides of the invention: column 1 references the SEQ ID NO; column 2 shows the number of amino acid residues in each polypeptide; column 3 shows potential phosphorylation sites; column 4 shows potential glycosylation sites; column 5 shows the amino acid residues comprising signature sequences and motifs; column 6 shows the identity of each polypeptide; and column 7 shows analytical methods and in some cases, searchable databases to which the analytical methods were applied. The methods of column 7 were used to characterize each polypeptide through sequence homology and protein motifs.

The columns of Table 3 show the tissue-specificity and diseases, disorders, or conditions associated with nucleotide sequences encoding MITP. The first column of Table 3 lists the nucleotide SEQ ID NOs. Column 2 lists tissue categories which express MITP as a fraction of total tissues expressing MITP. Column 3 lists diseases, disorders, or conditions associated with those tissues expressing MIP as a fraction of total tissues expressing MITP. Column 4 lists the vectors used to subclone each cDNA library. Of particular note are the expression of SEQ ID NO:13, SEQ ID NO:15, and SEQ ID NO:16. SEQ ID NO:13 is expressed in only 16 libraries, of which at least 9 (56%) are cell proliferative and at least 7 (44%) are associated with inflammation and immune response; 4 (25%) of these libraries are associated with reproductive tissue and 3 (19%) of these libraries are associated with hematopoietic/immune tissue. SEQ ID NO:15 is expressed in only 3 libraries, of which at least 2 (67%) are cell proliferative; 1 (33%) of these libraries is associated with reproductive tissue, 1 (33%) of these libraries is associated with cardiovascular tissue, and 1 (33%) of these libraries is associated with dermatologic tissue. SEQ ID NO:16 is expressed in only 1 library, a normalized fetal brain tissue library.

The columns of Table 4 show descriptions of the tissues used to construct the cDNA libraries from which cDNA clones encoding MITP were isolated. Column 1 references the nucleotide SEQ ID NOs, column 2 shows the cDNA libraries from which these clones were isolated, and column 3 shows the tissue origins and other descriptive information relevant to the cDNA libraries in column 2.

The following fragments of the nucleotide sequences encoding MITP are useful, for example, in hybridization or amplification technologies to identify SEQ ID NO:9–16 and to distinguish between SEQ ID NO:9–16 and related polynucleotide sequences. The useful fragments include the fragment of SEQ ID NO:9 from about nucleotide 34 to about nucleotide 78; the fragment of SEQ ID NO:10 from about nucleotide 732 to about nucleotide 776; the fragment of SEQ ID NO:11 from about nucleotide 8 to about nucleotide 52; the fragment of SEQ ID NO:12 from about nucleotide 97 to about nucleotide 141; the fragment of SEQ ID NO:13 from about nucleotide 228 to about nucleotide 272; the fragment of SEQ ID NO:14 from about nucleotide 38 to about nucleotide 82; the fragment of SEQ ID NO:15 from about nucleotide 61 to about nucleotide 105; and the fragment of SEQ ID NO:16 from about nucleotide 169 to about nucleotide 213. The polypeptides encoded by the specified fragments of SEQ ID NO:10–16 are useful, for example, as immunogenic peptides.

The invention also encompasses MITP variants. A preferred MITP variant is one which has at least about 80%, or alternatively at least about 90%, or even at least about 95% amino acid sequence identity to the MITP amino acid sequence, and which contains at least one functional or structural characteristic of MITP.

The invention also encompasses polynucleotides which encode MITP. In a particular embodiment, the invention encompasses a polynucleotide sequence comprising a sequence selected from the group consisting of SEQ ID NO:9–16, which encodes MITP. The polynucleotide sequences of SEQ ID NO:9–16, as presented in the Sequence Listing, embrace the equivalent RNA sequences, wherein occurrences of the nitrogenous base thymine are replaced with uracil, and the sugar backbone is composed of ribose instead of deoxyribose.

The invention also encompasses a variant of a polynucleotide sequence encoding MITP. In particular, such a variant polynucleotide sequence will have at least about 70%, or alternatively at least about 85%, or even at least about 95% polynucleotide sequence identity to the polynucleotide sequence encoding MITP. A particular aspect of the invention encompasses a variant of a polynucleotide sequence comprising a sequence selected from the group consisting of SEQ ID NO:9–16 which has at least about 70%, or alternatively at least about 85%, or even at least about 95% polynucleotide sequence identity to a nucleic acid sequence selected from the group consisting of SEQ ID NO:9–16. Any one of the polynucleotide variants described above can encode an amino acid sequence which contains at least one functional or structural characteristic of MITP.

It will be appreciated by those skilled in the art that as a result of the degeneracy of the genetic code, a multitude of polynucleotide sequences encoding MITP, some bearing minimal similarity to the polynucleotide sequences of any known and naturally occurring gene, may be produced. Thus, the invention contemplates each and every possible variation of polynucleotide sequence that could be made by selecting combinations based on possible codon choices. These combinations are made in accordance with the standard triplet genetic code as applied to the polynucleotide sequence of naturally occurring MITP, and all such variations are to be considered as being specifically disclosed.

Although nucleotide sequences which encode MITP and its variants are generally capable of hybridizing to the nucleotide sequence of the naturally occurring MITP under appropriately selected conditions of stringency, it may be advantageous to produce nucleotide sequences encoding MITP or its derivatives possessing a substantially different codon usage, e.g., inclusion of non-naturally occurring codons. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding MITP and its derivatives without altering the encoded amino acid sequences include the production of RNA transcripts having more desirable properties, such as a greater half-life, than transcripts produced from the naturally occurring sequence.

The invention also encompasses production of DNA sequences which encode MITP and MITP derivatives, or fragments thereof, entirely by synthetic chemistry. After production, the synthetic sequence may be inserted into any of the many available expression vectors and cell systems using reagents well known in the art. Moreover, synthetic chemistry may be used to introduce mutations into a sequence encoding MITP or any fragment thereof.

Also encompassed by the invention are polynucleotide sequences that are capable of hybridizing to the claimed polynucleotide sequences, and, in particular, to those shown in SEQ ID NO:9–16 and fragments thereof under various conditions of stringency. (See, e.g., Wahl, G. M. and S. L. Berger (1987) Methods Enzymol. 152:399407; Kimmel, A. R. (1987) Methods Enzymol. 152:507–511.) Hybridization conditions, including annealing and wash conditions, are described in "Definitions."

Methods for DNA sequencing are well known in the art and may be used to practice any of the embodiments of the invention. The methods may employ such enzymes as the Klenow fragment of DNA polymerase I, SEQUENASE (US Biochemical, Cleveland Ohio), Taq polymerase (Perkin-Elmer), thermostable T7 polymerase (Amersham Pharmacia Biotech, Piscataway N.J.), or combinations of polymerases and proofreading exonucleases such as those found in the ELONGASE amplification system (Life Technologies, Gaithersburg Md.). Preferably, sequence preparation is automated with machines such as the MICROLAB 2200 liquid transfer system (Hamilton, Reno Nev.), PTC200 thermal cycler (MJ Research, Watertown Mass.) and ABI CATALYST 800 thermal cycler (Perkin-Elmer). Sequencing is then carried out using either the ABI 373 or 377 DNA sequencing system (Perkin-Elmer), the MEGABACE 1000 DNA sequencing system (Molecular Dynamics, Sunnyvale Calif.), or other systems known in the art. The resulting sequences are analyzed using a variety of algorithms which are well known in the art. (See, e.g., Ausubel, F. M. (1997) *Short Protocols in Molecular Biology*, John Wiley & Sons, New York N.Y., unit 7.7; Meyers, R. A. (1995) *Molecular Biology and Biotechnology*, Wiley VCH, New York N.Y., pp. 856–853.)

The nucleic acid sequences encoding MITP may be extended utilizing a partial nucleotide sequence and employing various PCR-based methods known in the art to detect upstream sequences, such as promoters and regulatory elements. For example, one method which may be employed, restriction-site PCR, uses universal and nested primers to amplify unknown sequence from genomic DNA within a cloning vector. (See, e.g., Sarkar, G. (1993) PCR Methods Applic. 2:318–322.) Another method, inverse PCR, uses primers that extend in divergent directions to amplify unknown sequence from a circularized template. The template is derived from restriction fragments comprising a known genomic locus and surrounding sequences. (See, e.g., Triglia, T. et al. (1988) Nucleic Acids Res. 16:8186.) A third method, capture PCR, involves PCR amplification of DNA fragments adjacent to known sequences in human and yeast artificial chromosome DNA. (See, e.g., Lagerstrom, M. et al. (1991) PCR Methods Applic. 1:111–119.) In this method, multiple restriction enzyme digestions and ligations may be used to insert an engineered double-stranded sequence into a region of unknown sequence before performing PCR. Other methods which may be used to retrieve unknown sequences are known in the art. (See, e.g., Parker, J. D. et al. (1991) Nucleic Acids Res. 19:3055–3060). Additionally, one may use PCR, nested primers, and PROMOTERFINDER libraries (Clontech, Palo Alto Calif.) to walk genomic DNA. This procedure avoids the need to screen libraries and is useful in finding intron/exon junctions. For all PCR-based methods, primers may be designed using commercially available software, such as OLIGO 4.06 Primer Analysis software (National Biosciences, Plymouth Minn.) or another appropriate program, to be about 22 to 30 nucleotides in length, to have a GC content of about 50% or more, and to anneal to the template at temperatures of about 68° C. to 72° C.

When screening for full-length cDNAs, it is preferable to use libraries that have been size-selected to include larger cDNAs. In addition, random-primed libraries, which often include sequences containing the 5' regions of genes, are preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different nucleotide-specific, laser-stimulated fluorescent dyes, and a charge coupled device camera for detection of the emitted wavelengths. Output/light intensity may be converted to electrical signal using appropriate software (e.g., GENOTYPER and SEQUENCE NAVIGATOR, Perkin-Elmer), and the entire process from loading of samples to computer analysis and electronic data display may be computer controlled. Capillary electrophoresis is especially preferable for sequencing small DNA fragments which may be present in limited amounts in a particular sample.

In another embodiment of the invention, polynucleotide sequences or fragments thereof which encode MITP may be cloned in recombinant DNA molecules that direct expression of MITP, or fragments or functional equivalents thereof, in appropriate host cells. Due to the inherent degeneracy of the genetic code, other DNA sequences which encode substantially the same or a functionally equivalent amino acid sequence may be produced and used to express MITP.

The nucleotide sequences of the present invention can be engineered using methods generally known in the art in order to alter MITP-encoding sequences for a variety of purposes including, but not limited to, modification of the cloning, processing, and/or expression of the gene product. DNA shuffling by random fragmentation and PCR reassembly of gene fragments and synthetic oligonucleotides may be used to engineer the nucleotide sequences. For example, oligonucleotide-mediated site-directed mutagenesis may be used to introduce mutations that create new restriction sites, alter glycosylation patterns, change codon preference, produce splice variants, and so forth.

The nucleotides of the present invention may be subjected to DNA shuffling techniques such as MOLECULARBREEDING (Maxygen Inc., Santa Clara Calif.; described in U.S. Pat. No. 5,837,458; Chang, C.-C. et al. (1999) Nat. Biotechnol. 17:793–797; Christians, F. C. et al. (1999) Nat. Biotechnol. 17:259–264; and Crameri, A. et al. (1996) Nat. Biotechnol. 14:315–319) to alter or improve the biological properties of MITP, such as its biological or enzymatic activity or its ability to bind to other molecules or compounds. DNA shuffling is a process by which a library of gene variants is produced using PCR-mediated recombination of gene fragments. The library is then subjected to selection or screening procedures that identify those gene variants with the desired properties. These preferred variants may then be pooled and further subjected to recursive rounds of DNA shuffling and selection/screening. Thus, genetic diversity is created through "artificial" breeding and rapid molecular evolution. For example, fragments of a single gene containing random point mutations may be recombined, screened, and then reshuffled until the desired properties are optimized. Alternatively, fragments of a given gene may be recombined with fragments of homologous genes in the same gene family, either from the same or different species, thereby maximizing the genetic diversity of multiple naturally occurring genes in a directed and controllable manner.

In another embodiment, sequences encoding MITP may be synthesized, in whole or in part, using chemical methods well known in the art. (See, e.g., Caruthers, M. H. et al. (1980) Nucleic Acids Symp. Ser. 7:215–223; and Horn, T. et al. (1980) Nucleic Acids Symp. Ser. 7:225–232.) Alternatively, MITP itself or a fragment thereof may be synthesized using chemical methods. For example, peptide synthesis can be performed using various solid-phase techniques. (See, e.g., Roberge, J. Y. et al. (1995) Science 269:202–204.) Automated synthesis may be achieved using the ABI peptide synthesizer (Perkin-Elmer). Additionally, the amino acid sequence of MITP, or any part thereof, may be altered during direct synthesis and/or combined with sequences from other proteins, or any part thereof, to produce a variant polypeptide.

The peptide may be substantially purified by preparative high performance liquid chromatography. (See, e.g., Chiez, R. M. and F. Z. Regnier (1990) Methods Enzymol. 182: 392–421.) The composition of the synthetic peptides may be confirmed by amino acid analysis or by sequencing. (See, e.g., Creighton, T. (1984) *Proteins, Structures and Molecular Properties*, W H Freeman, New York N.Y.)

In order to express a biologically active MITP, the nucleotide sequences encoding MITP or derivatives thereof may be inserted into an appropriate expression vector, i.e., a vector which contains the necessary elements for transcriptional and translational control of the inserted coding sequence in a suitable host. These elements include regulatory sequences, such as enhancers, constitutive and inducible promoters, and 5' and 3' untranslated regions in the vector and in polynucleotide sequences encoding MITP. Such elements may vary in their strength and specificity. Specific initiation signals may also be used to achieve more efficient translation of sequences encoding MITP. Such signals include the ATG initiation codon and adjacent sequences, e.g. the Kozak sequence. In cases where sequences encoding MITP and its initiation codon and upstream regulatory sequences are inserted into the appropriate expression vector, no additional transcriptional or translational control signals may be needed. However, in cases where only coding sequence, or a fragment thereof, is inserted, exogenous translational control signals including an in-frame ATG initiation codon should be provided by the vector. Exogenous translational elements and initiation codons may be of various origins, both natural and synthetic. The efficiency of expression may be enhanced by the inclusion of enhancers appropriate for the particular host cell system used. (See, e.g., Scharf, D. et al. (1994) Results Probl. Cell Differ. 20:125–162.)

Methods which are well known to those skilled in the art may be used to construct expression vectors containing sequences encoding MITP and appropriate transcriptional and translational control elements. These methods include in vitro recombinant DNA techniques, synthetic techniques, and in vivo genetic recombination. (See, e.g., Sambrook, J. et al. (1989) *Molecular Cloning, A Laboratory Manual*, Cold Spring Harbor Press, Plainview N.Y., ch. 4, 8, and 16–17; Ausubel, F. M. et al. (1995) *Current Protocols in Molecular Biology*, John Wiley & Sons, New York N.Y., ch. 9, 13, and 16.)

A variety of expression vector/host systems may be utilized to contain and express sequences encoding MITP. These include, but are not limited to, microorganisms such as bacteria transformed with recombinant bacteriophage, plasmid, or cosmid DNA expression vectors; yeast transformed with yeast expression vectors; insect cell systems infected with viral expression vectors (e.g., baculovirus); plant cell systems transformed with viral expression vectors (e.g., cauliflower mosaic virus, CaMV, or tobacco mosaic virus, TMV) or with bacterial expression vectors (e.g., Ti or pBR322 plasmids); or animal cell systems. The invention is not limited by the host cell employed.

In bacterial systems, a number of cloning and expression vectors may be selected depending upon the use intended for polynucleotide sequences encoding MITP. For example, routine cloning, subcloning, and propagation of polynucleotide sequences encoding MITP can be achieved using a multifunctional *E. coli* vector such as PBLUESCRIPT (Stratagene, La Jolla Calif.) or PSPORT1 plasmid (Life Technologies). Ligation of sequences encoding MITP into the vector's multiple cloning site disrupts the lacZ gene, allowing a colorimetric screening procedure for identification of transformed bacteria containing recombinant molecules. In addition, these vectors may be useful for in vitro transcription, dideoxy sequencing, single strand rescue with helper phage, and creation of nested deletions in the cloned sequence. (See, e.g., Van Heeke, G. and S. M. Schuster (1989) J. Biol. Chem. 264:5503–5509.) When large quantities of MITP are needed, e.g. for the production of antibodies, vectors which direct high level expression of MITP may be used. For example, vectors containing the strong, inducible T5 or T7 bacteriophage promoter may be used.

Yeast expression systems may be used for production of MITP. A number of vectors containing constitutive or inducible promoters, such as alpha factor, alcohol oxidase, and PGH promoters, may be used in the yeast *Saccharomyces cerevisiae* or *Pichia Dastoris*. In addition, such vectors direct either the secretion or intracellular retention of expressed proteins and enable integration of foreign sequences into the host genome for stable propagation. (See, e.g., Ausubel, 1995, supra; Bitter, G. A, et al. (1987) Methods Enzymol. 153:516–544; and Scorer, C. A. et al. (1994) Bio/Technology 12:181–184.)

Plant systems may also be used for expression of MITP. Transcription of sequences encoding MITP may be driven viral promoters, e.g., the 35S and 19S promoters of CaMV used alone or in combination with the omega leader sequence from TMV (Takamatsu, N. (1987) EMBO J. 6:307–311). Alternatively, plant promoters such as the small subunit of RUBISCO or heat shock promoters may be used. (See, e.g., Coruzzi, G. et al. (1984) EMBO J. 3:1671–1680; Broglie, R. et al. (1984) Science 224:838–843; and Winter, J. et al. (1991) Results Probl. Cell Differ. 17:85–105.) These constructs can be introduced into plant cells by direct DNA transformation or pathogen-mediated transfection. (See, e.g., *The McGraw Hill Yearbook of Science and Technology* (1992) McGraw Hill, New York N.Y., pp. 191–196.)

In mammalian cells, a number of viral-based expression systems may be utilized. In cases where an adenovirus is used as an expression vector, sequences encoding MITP may be ligated into an adenovirus transcription/translation complex consisting of the late promoter and tripartite leader sequence. Insertion in a non-essential E1 or E3 region of the viral genome may be used to obtain infective virus which expresses MITP in host cells. (See, e.g., Logan, J. and T. Shenk (1984) Proc. Natl. Acad. Sci. USA 81:3655–3659.) In addition, transcription enhancers, such as the Rous sarcoma virus (RSV) enhancer, may be used to increase expression in mammalian host cells. SV40 or EBV-based vectors may also be used for high-level protein expression.

Human artificial chromosomes (HACs) may also be employed to deliver larger fragments of DNA than can be contained in and expressed from a plasmid. HACs of about 6 kb to 10 Mb are constructed and delivered via conventional delivery methods (liposomes, polycationic amino polymers, or vesicles) for therapeutic purposes. (See, e.g., Harrington, J. J. et al. (1997) Nat. Genet. 15:345–355.)

For long term production of recombinant proteins in mammalian systems, stable expression of MITP in cell lines is preferred. For example, sequences encoding MITP can be transformed into cell lines using expression vectors which may contain viral origins of replication and/or endogenous expression elements and a selectable marker gene on the same or on a separate vector. Following the introduction of the vector, cells may be allowed to grow for about 1 to 2 days in enriched media before being switched to selective media. The purpose of the selectable marker is to confer resistance to a selective agent, and its presence allows growth and recovery of cells which successfully express the introduced sequences. Resistant clones of stably transformed cells may be propagated using tissue culture techniques appropriate to the cell type.

Any number of selection systems may be used to recover transformed cell lines. These include, but are not limited to, the herpes simplex virus thymidine kinase and adenine phosphoribosyltransferase genes, for use in tk and apr cells, respectively. (See, e.g., Wigler, M. et al. (1977) Cell 11:223–232; Lowy, I. et al. (1980) Cell 22:817–823.) Also, antimetabolite, antibiotic, or herbicide resistance can be used as the basis for selection. For example, dhfr confers resistance to methotrexate; neo confers resistance to the aminoglycosides neomycin and G418; and als and pat confer resistance to chlorsulfuron and phosphinotricin acetyltransferase, respectively. (See, e.g., Wigler, M. et al. (1980) Proc. Natl. Acad. Sci. USA 77:3567–3570; Colbere-Garapin, F. et al. (1981) J. Mol. Biol. 150:1–14.) Additional selectable genes have been described, e.g., trpB and hisD, which alter cellular requirements for metabolites. (See, e.g., Hartman, S. C. and R. C. Mulligan (1988) Proc. Natl. Acad. Sci. USA 85:8047–8051.) Visible markers, e.g., anthocyanins, green fluorescent proteins (GFP; Clontech), βglucuronidase and its substrate β-glucuronide, or luciferase and its substrate luciferin may be used. These markers can be used not only to identify transformants, but also to quantify the amount of transient or stable protein expression attributable to a specific vector system. (See, e.g., Rhodes, C. A. (1995) Methods Mol. Biol. 55:121–131.)

Although the presence/absence of marker gene expression suggests that the gene of interest is also present, the presence and expression of the gene may need to be confirmed. For example, if the sequence encoding MITP is inserted within a marker gene sequence, transformed cells containing sequences encoding MITP can be identified by the absence of marker gene function. Alternatively, a marker gene can be placed in tandem with a sequence encoding MITP under the control of a single promoter. Expression of the marker gene in response to induction or selection usually indicates expression of the tandem gene as well.

In general, host cells that contain the nucleic acid sequence encoding MITP and that express MITP may be identified by a variety of procedures known to those of skill in the art. These procedures include, but are not limited to, DNA—DNA or DNA-RNA hybridizations, PCR amplification, and protein bioassay or immunoassay techniques which include membrane, solution, or chip based technologies for the detection and/or quantification of nucleic acid or protein sequences.

Immunological methods for detecting and measuring the expression of MITP using either specific polyclonal or monoclonal antibodies are known in the art. Examples of such techniques include enzyme-linked immunosorbent assays (ELISAs), radioimmunoassays (RIAs), and fluorescence activated cell sorting (FACS). A two-site, monoclonal-based immunoassay utilizing monoclonal antibodies reactive to two non-interfering epitopes on MITP is preferred, but a competitive binding assay may be employed. These and other assays are well known in the art. (See, e.g., Hampton, R. et al. (1990) Serological Methods, a Laboratory Manual, APS Press, St. Paul Minn., Sect. IV; Coligan, J. E. et al. (1997) Current Protocols in Immunology, Greene Pub. Associates and Wiley-Interscience, New York N.Y.; and Pound, J. D. (1998) Immunochemical Protocols, Humana Press, Totowa N.J.)

A wide variety of labels and conjugation techniques are known by those skilled in the art and may be used in various nucleic acid and amino acid assays. Means for producing labeled hybridization or PCR probes for detecting sequences related to polynucleotides encoding MITP include oligolabeling, nick translation, end-labeling, or PCR amplification using a labeled nucleotide. Alternatively, the sequences encoding MITP, or any fragments thereof, may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits, such as those provided by Amersham Pharmacia Biotech, Promega (Madison Wis.), and US Biochemical. Suitable reporter molecules or labels which may be used for ease of detection include radionuclides, enzymes, fluorescent, chemiluminescent, or chromogenic agents, as well as substrates, cofactors, inhibitors, magnetic particles, and the like.

Host cells transformed with nucleotide sequences encoding MITP may be cultured under conditions suitable for the expression and recovery of the protein from cell culture. The protein produced by a transformed cell may be secreted or retained intracellularly depending on the sequence and/or the vector used. As will be understood by those of skill in the art, expression vectors containing polynucleotides which encode MITP may be designed to contain signal sequences which direct secretion of MITP through a prokaryotic or eukaryotic cell membrane.

In addition, a host cell strain may be chosen for its ability to modulate expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" or "pro" form of the protein may also be used to specify protein targeting, folding, and/or activity. Different host cells which have specific cellular machinery and characteristic mechanisms for post-translational activities (e.g., CHO, HeLa, MDCK, HEK293, and W138) are available from the American Type Culture Collection (ATCC, Manassas Va.) and may be chosen to ensure the correct modification and processing of the foreign protein.

In another embodiment of the invention, natural, modified, or recombinant nucleic acid sequences encoding MITP may be ligated to a heterologous sequence resulting in translation of a fusion protein in any of the aforementioned host systems. For example, a chimeric MITP protein containing a heterologous moiety that can be recognized by a commercially available antibody may facilitate the screening of peptide libraries for inhibitors of MITP activity. Heterologous protein and peptide moieties may also facilitate purification of fusion proteins using commercially available affinity matrices. Such moieties include, but are not limited to, glutathione S-transferase (GST), maltose binding protein (MBP), thioredoxin (Trx), calmodulin binding peptide (CBP), 6-His, FLAG, c-myc, and hemagglutinin (HA). GST, MBP, Trx, CBP, and 6-His enable purification of their cognate fusion proteins on immobilized glutathione, maltose, phenylarsine oxide, calmodulin, and metal-chelate resins, respectively. FLAG, c-myc, and hemagglutinin (HA) enable immunoaffinity purification of fusion proteins using commercially available monoclonal and polyclonal antibodies that specifically recognize these epitope tags. A fusion protein may also be engineered to contain a proteolytic cleavage site located between the MITP encoding sequence and the heterologous protein sequence, so that MITP may be cleaved away from the heterologous moiety following purification. Methods for fusion protein expression and purification are discussed in Ausubel (1995, supra, ch. 10). A variety of commercially available kits may also be used to facilitate expression and purification of fusion proteins.

In a further embodiment of the invention, synthesis of radiolabeled MITP may be achieved in vitro using the TNT rabbit reticulocyte lysate or wheat germ extract system (Promega). These systems couple transcription and translation of protein-coding sequences operably associated with the T7, T3, or SP6 promoters. Translation takes place in the presence of a radiolabeled amino acid precursor, for example, $^{35}$S-methionine.

Fragments of MITP may be produced not only by recombinant means, but also by direct peptide synthesis using solid-phase techniques. (See, e.g., Creighton, supra. pp. 55–60.) Protein synthesis may be performed by manual techniques or by automation. Automated synthesis may be achieved, for example, using the ABI 431A peptide synthesizer (Perkin-Elmer). Various fragments of MITP may be synthesized separately and then combined to produce the full length molecule.

Therapeutics

Chemical and structural similarity, e.g., in the context of sequences and motifs, exists between regions of MITP and mitochondrial proteins. In addition, the expression of MITP is closely associated with disorders of cell proliferation, inflammation, and immune response. Therefore, MITP appears to play a role in disorders of cell proliferation, inflammation, and immune response. In the treatment of disorders associated with increased MITP expression or activity, it is desirable to decrease the expression or activity of MITP. In the treatment of disorders associated with decreased MITP expression or activity, it is desirable to increase the expression or activity of MITP.

Therefore, in one embodiment, MITP or a fragment or derivative thereof may be administered to a subject to treat or prevent a disorder associated with decreased expression or activity of MITP. Examples of such disorders include, but are not limited to, a disorder of cell proliferation such as actinic keratosis, arteriosclerosis, atherosclerosis, bursitis, cirrhosis, hepatitis, mixed connective tissue disease (MCTD), myelofibrosis, paroxysmal nocturnal hemoglobinuria, polycythemia vera, psoriasis, primary thrombocythemia, and cancers including adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; and an autoimmune/inflammatory disorder such as acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, autoimmune polyenodocrinopathy-candidiasis-ectodermal dystrophy (APECED), bronchitis, cholecystitis, contact dermatitis, Crohn's disease, atopic dermatitis, dermatomyositis, diabetes mellitus, emphysema, episodic lymphopenia with lymphocytotoxins, erythroblastosis fetalis, erythema nodosum, atrophic gastritis, glomerulonephritis, Goodpasture's syndrome, gout, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polymyositis, psoriasis, Reiter's syndrome, rheumatoid arthritis, scleroderma, Sjögren's syndrome, systemic anaphylaxis, systemic lupus erythematosus, systemic sclerosis, thrombocytopenic purpura, ulcerative colitis, uveitis, Werner syndrome, complications of cancer, hemodialysis, and extracorporeal circulation; viral, bacterial, fungal, parasitic, protozoal, and helminthic infections; and trauma.

In another embodiment, a vector capable of expressing MITP or a fragment or derivative thereof may be administered to a subject to treat or prevent a disorder associated with decreased expression or activity of MITP including, but not limited to, those described above.

In a further embodiment, a pharmaceutical composition comprising a substantially purified MITP in conjunction with a suitable pharmaceutical carrier may be administered to a subject to treat or prevent a disorder associated with decreased expression or activity of MITP including, but not limited to, those provided above.

In still another embodiment, an agonist which modulates the activity of MITP may be administered to a subject to treat or prevent a disorder associated with decreased expression or activity of MITP including, but not limited to, those listed above.

In a further embodiment, an antagonist of MITP may be administered to a subject to treat or prevent a disorder associated with increased expression or activity of MITP. Examples of such disorders include, but are not limited to, those disorders of cell proliferation, inflammation, and immune response described above. In one aspect, an antibody which specifically binds MITP may be used directly as an antagonist or indirectly as a targeting or delivery mechanism for bringing a pharmaceutical agent to cells or tissues which express MITP.

In an additional embodiment, a vector expressing the complement of the polynucleotide encoding MITP may be administered to a subject to treat or prevent a disorder associated with increased expression or activity of MITP including, but not limited to, those described above.

In other embodiments, any of the proteins, antagonists, antibodies, agonists, complementary sequences, or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of MITP may be produced using methods which are generally known in the art. In particular, purified MITP may be used to produce antibodies or to screen libraries of pharmaceutical agents to identify those which specifically bind MITP. Antibodies to MITP may also be generated using methods that are well known in the art. Such antibodies may include, but are not limited to, polyclonal, monoclonal, chimeric, and single chain antibodies, Fab fragments, and fragments produced by a Fab expression library. Neutralizing antibodies (i.e., those which inhibit dimer formation) are generally preferred for therapeutic use.

For the production of antibodies, various hosts including goats, rabbits, rats, mice, humans, and others may be immunized by injection with MITP or with any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, KLH, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to MITP have an amino acid sequence consisting of at least about 5 amino acids, and generally will consist of at least about 10 amino acids. It is also preferable that these oligopeptides, peptides, or fragments are identical to a portion of the amino acid sequence of the natural protein and contain the entire amino acid sequence of a small, naturally occurring molecule. Short stretches of MITP amino acids may be fused with those of another protein, such as KLH, and antibodies to the chimeric molecule may be produced.

Monoclonal antibodies to MITP may be prepared using any technique which provides for the production of antibody molecules by continuous cell lines in culture. These include, but are not limited to, the hybridoma technique, the human B-cell hybridoma technique, and the EBV-hybridoma technique. (See, e.g., Kohler, G. et al. (1975) Nature 256: 495–497; Kozbor, D. et al. (1985) J. Immunol. Methods 81:31–42; Cote, R. J. et al. (1983) Proc. Natl. Acad. Sci. USA 80:2026–2030; and Cole, S. P. et al. (1984) Mol. Cell Biol. 62:109–120.)

In addition, techniques developed for the production of "chimeric antibodies," such as the splicing of mouse antibody genes to human antibody genes to obtain a molecule with appropriate antigen specificity and biological activity, can be used. (See, e.g., Morrison, S. L. et al. (1984) Proc. Natl. Acad. Sci. USA 81:6851–6855; Neuberger, M. S. et al. (1984) Nature 312:604–608; and Takeda, S. et al. (1985) Nature 314:452–454.) Alternatively, techniques described for the production of single chain antibodies may be adapted, using methods known in the art, to produce MITP-specific single chain antibodies. Antibodies with related specificity, but of distinct idiotypic composition, may be generated by chain shuffling from random combinatorial immunoglobulin libraries. (See, e.g., Burton, D. R. (1991) Proc. Natl. Acad. Sci. USA 88:10134–10137.)

Antibodies may also be produced by inducing in vivo production in the lymphocyte population or by screening immunoglobulin libraries or panels of highly specific binding reagents as disclosed in the literature. (See, e.g., Orlandi, R. et al. (1989) Proc. Natl. Acad. Sci. USA 86:3833–3837; Winter, G. et al. (1991) Nature 349:293–299.)

Antibody fragments which contain specific binding sites for MITP may also be generated. For example, such fragments include, but are not limited to, F(ab')$_2$ fragments produced by pepsin digestion of the antibody molecule and Fab fragments generated by reducing the disulfide bridges of the F(ab')2 fragments. Alternatively, Fab expression libraries may be constructed to allow rapid and easy identification of monoclonal Fab fragments with the desired specificity. (See, e.g., Huse, W. D. et al. (1989) Science 246:1275–1281.)

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between MITP and its specific antibody. A two-site, monoclonal-based immunoassay utilizing monoclonal antibodies reactive to two non-interfering MITP epitopes is generally used, but a competitive binding assay may also be employed (Pound, supra).

Various methods such as Scatchard analysis in conjunction with radioimmunoassay techniques may be used to assess the affinity of antibodies for MITP. Affinity is expressed as an association constant, $K_a$, which is defined as the molar concentration of MITP-antibody complex divided by the molar concentrations of free antigen and free antibody under equilibrium conditions. The $K_a$ determined for a preparation of polyclonal antibodies, which are heterogeneous in their affinities for multiple MITP epitopes, represents the average affinity, or avidity, of the antibodies for MITP. The $K_a$ determined for a preparation of monoclonal antibodies, which are monospecific for a particular MITP epitope, represents a true measure of affinity. High-affinity antibody preparations with $K_a$ ranging from about $10^9$ to $10^{12}$ L/mole are preferred for use in immunoassays in which the MITP-antibody complex must withstand rigorous manipulations. Low-affinity antibody preparations with $K_a$ ranging from about $10^6$ to $10^7$ L/mole are preferred for use in immunopurification and similar procedures which ultimately require dissociation of MIT, preferably in active form, from the antibody (Catty, D. (1988) *Antibodies, Volume I: A Practical Approach*, IRL Press, Washington, D.C.; Liddell, J. E. and Cryer, A. (1991) A Practical Guide to Monoclonal Antibodies, John Wiley & Sons, New York N.Y.).

The titer and avidity of polyclonal antibody preparations may be further evaluated to determine the quality and suitability of such preparations for certain downstream applications. For example, a polyclonal antibody preparation containing at least 1–2 mg specific antibody/ml, preferably 5–10 mg specific antibody/ml, is generally employed in procedures requiring precipitation of MITP-antibody complexes. Procedures for evaluating antibody specificity, titer, and avidity, and guidelines for antibody quality and usage in various applications, are generally available. (See, e.g., Catty, supra, and Coligan et al. supra.)

In another embodiment of the invention, the polynucleotides encoding MITP, or any fragment or complement thereof, may be used for therapeutic purposes. In one aspect, the complement of the polynucleotide encoding MITP may be used in situations in which it would be desirable to block the transcription of the mRNA. In particular, cells may be transformed with sequences complementary to polynucleotides encoding MITP. Thus, complementary molecules or fragments may be used to modulate MITP activity, or to achieve regulation of gene function. Such technology is now well known in the art, and sense or antisense oligonucleotides or larger fragments can be designed from various locations along the coding or control regions of sequences encoding MITP.

Expression vectors derived from retroviruses, adenoviruses, or herpes or vaccinia viruses, or from various bacterial plasmids, may be used for delivery of nucleotide sequences to the targeted organ, tissue, or cell population. Methods which are well known to those skilled in the art can be used to construct vectors to express nucleic acid sequences complementary to the polynucleotides encoding MITP. (See, e.g., Sambrook, supra; Ausubel, 1995, supra.)

Genes encoding MITP can be turned off by transforming a cell or tissue with expression vectors which express high levels of a polynucleotide, or fragment thereof, encoding MITP. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector, and may last even longer if appropriate replication elements are part of the vector system.

As mentioned above, modifications of gene expression can be obtained by designing complementary sequences or antisense molecules (DNA, RNA, or PNA) to the control, 5', or regulatory regions of the gene encoding MITP. Oligonucleotides derived from the transcription initiation site, e.g., between about positions −10 and +10 from the start site, may be employed Similarly, inhibition can be achieved using triple helix base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature. (See, e.g., Gee, J. E. et al. (1994) in Huber, B. E. and B. I. Carr, *Molecular and Immunologic Approaches*, Futura Publishing, Mt. Kisco N.Y., pp. 163–177.) A complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. For example, engineered hammerhead motif ribozyme molecules may specifically and efficiently catalyze endonucleolytic cleavage of sequences encoding MITP.

Specific ribozyme cleavage sites within any potential RNA target are initially identified by scanning the target molecule for ribozyme cleavage sites, including the following sequences: GUA, GUU, and GUC. Once identified, short RNA sequences of between 15 and 20 ribonucleotides, corresponding to the region of the target gene containing the cleavage site, may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding MITP. Such DNA sequences may be incorporated into a wide variety of vectors with suitable RNA polymerase promoters such as T7 or SP6. Alternatively, these cDNA constructs that synthesize complementary RNA, constitutively or inducibly, can be introduced into cell lines, cells, or tissues.

RNA molecules may be modified to increase intracellular stability and half-life. Possible modifications include, but are not limited to, the addition of flanking sequences at the 5' and/or 3' ends of the molecule, or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections, or by polycationic amino polymers may be achieved using methods which are well known in the art. (See, e.g., Goldman, C. K. et al. (1997) Nat. Biotechnol. 15:462–466.)

Any of the therapeutic methods described above may be applied to any subject in need of such therapy, including, for example, mammals such as humans, dogs, cats, cows, horses, rabbits, and monkeys.

An additional embodiment of the invention relates to the administration of a pharmaceutical or sterile composition, in conjunction with a pharmaceutically acceptable carrier, for any of the therapeutic effects discussed above. Such pharmaceutical compositions may consist of MITP, antibodies to MITP, and mimetics, agonists, antagonists, or inhibitors of MITP. The compositions may be administered alone or in combination with at least one other agent, such as a stabilizing compound, which may be administered in any sterile, biocompatible pharmaceutical carrier including, but not limited to, saline, buffered saline, dextrose, and water. The compositions may be administered to a patient alone, or in combination with other agents, drugs, or hormones.

The pharmaceutical compositions utilized in this invention may be administered by any number of routes including, but not limited to, oral, intravenous, intramuscular, intraarterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing, Easton Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combining active compounds with solid excipient and processing the resultant mixture of granules (optionally, after grinding) to obtain tablets or dragee cores. Suitable auxiliaries can be added, if desired. Suitable excipients include carbohydrate or protein fillers, such as sugars, including lactose, sucrose, mannitol, and sorbitol; starch from corn, wheat, rice, potato, or other plants; cellulose, such as methyl cellulose, hydroxypropylmethyl-cellulose, or sodium carboxymethylcellulose; gums, including arabic and tragacanth; and proteins, such as gelatin and collagen. If desired, disintegrating or solubilizing agents may be added, such as the cross-linked polyvinyl pyrrolidone, agar, and alginic acid or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with fillers or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also contain suitable stabilizers or agents to increase the solubility of the compounds and allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, and succinic acids. Salts tend to be more soluble in aqueous or other protonic solvents than are the corresponding free base forms. In other cases, the preparation may be a lyophilized powder which may contain any or all of the following: 1 mM to 50 mM histidine, 0.1% to 2% sucrose, and 2% to 7% mannitol, at a pH range of 4.5 to 5.5, that is combined with buffer prior to use.

After pharmaceutical compositions have been prepared, they can be placed in an appropriate container and labeled for treatment of an indicated condition. For administration of MITP, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells, or in animal models such as mice, rats, rabbits, dogs, or pigs. An animal model may also be used to determine the appropriate concentration range and route of administration. Such information can then be used to determine useful doses and routes for administration in humans.

A therapeutically effective dose refers to that amount of active ingredient, for example MITP or fragments thereof, antibodies of MITP, and agonists, antagonists or inhibitors of MITP, which ameliorates the symptoms or condition. Therapeutic efficacy and toxicity may be determined by standard pharmaceutical procedures in cell cultures or with experimental animals, such as by calculating the $ED_{50}$ (the dose therapeutically effective in 50% of the population) or $LD_{50}$ (the dose lethal to 50% of the population) statistics. The dose ratio of toxic to therapeutic effects is the therapeutic index, which can be expressed as the $LD_{50}/ED_{50}$ ratio. Pharmaceutical compositions which exhibit large therapeutic indices are preferred. The data obtained from cell culture assays and animal studies are used to formulate a range of dosage for human use. The dosage contained in such compositions is preferably within a range of circulating concentrations that includes the $ED_{50}$ with little or no toxicity. The dosage varies within this range depending upon the dosage form employed, the sensitivity of the patient, and the route of administration.

The exact dosage will be determined by the practitioner, in light of factors related to the subject requiring treatment. Dosage and administration are adjusted to provide sufficient levels of the active moiety or to maintain the desired effect. Factors which may be taken into account include the severity of the disease state, the general health of the subject, the age, weight, and gender of the subject, time and frequency of administration, drug combination(s), reaction sensitivities, and response to therapy. Long-acting pharmaceutical compositions may be administered every 3 to 4 days, every week, or biweekly depending on the half-life and clearance rate of the particular formulation.

Normal dosage amounts may vary from about 0.1 µg to 100,000 µg, up to a total dose of about 1 gram, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Diagnostics

In another embodiment, antibodies which specifically bind MITP may be used for the diagnosis of disorders characterized by expression of MITP, or in assays to monitor patients being treated with MITP or agonists, antagonists, or inhibitors of MITP. Antibodies useful for diagnostic purposes may be prepared in the same manner as described above for therapeutics. Diagnostic assays for MITP include methods which utilize the antibody and a label to detect MITP in human body fluids or in extracts of cells or tissues. The antibodies may be used with or without modification, and may be labeled by covalent or non-covalent attachment of a reporter molecule. A wide variety of reporter molecules, several of which are described above, are known in the art and may be used.

A variety of protocols for measuring MITP, including ELISAs, RIAs, and FACS, are known in the art and provide a basis for diagnosing altered or abnormal levels of MITP expression. Normal or standard values for MITP expression are established by combining body fluids or cell extracts taken from normal mammalian subjects, for example, human subjects, with antibody to MITP under conditions suitable for complex formation. The amount of standard complex formation may be quantitated by various methods, such as photometric means. Quantities of MITP expressed in subject, control, and disease samples from biopsied tissues are compared with the standard values. Deviation between standard and subject values establishes the parameters for diagnosing disease.

In another embodiment of the invention, the polynucleotides encoding MITP may be used for diagnostic purposes. The polynucleotides which may be used include oligonucleotide sequences, complementary RNA and DNA molecules, and PNAs. The polynucleotides may be used to detect and quantify gene expression in biopsied tissues in which expression of MITP may be correlated with disease. The diagnostic assay may be used to determine absence, presence, and excess expression of MITP, and to monitor regulation of MITP levels during therapeutic intervention.

In one aspect, hybridization with PCR probes which are capable of detecting polynucleotide sequences, including genomic sequences, encoding MITP or closely related molecules may be used to identify nucleic acid sequences which encode MITP. The specificity of the probe, whether it is made from a highly specific region, e.g., the 5' regulatory region, or from a less specific region, e.g., a conserved motif, and the stringency of the hybridization or amplification will determine whether the probe identifies only naturally occurring sequences encoding MITP, allelic variants, or related sequences.

Probes may also be used for the detection of related sequences, and may have at least 50% sequence identity to any of the MITP encoding sequences. The hybridization probes of the subject invention may be DNA or RNA and may be derived from the sequence of SEQ ID NO:9–16 or from genomic sequences including promoters, enhancers, and introns of the MITP gene.

Means for producing specific hybridization probes for DNAs encoding MITP include the cloning of polynucleotide sequences encoding MITP or MITP derivatives into vectors for the production of mRNA probes. Such vectors are known in the art, are commercially available, and may be used to synthesize RNA probes in vitro by means of the addition of the appropriate RNA polymerases and the appropriate labeled nucleotides. Hybridization probes may be labeled by a variety of reporter groups, for example, by radionuclides such as $^{32}P$ or $^{35}S$, or by enzymatic labels, such as alkaline phosphatase coupled to the probe via avidin/biotin coupling systems, and the like.

Polynucleotide sequences encoding MITP may be used for the diagnosis of disorders associated with expression of MITP. Examples of such disorders include, but are not limited to, a disorder of cell proliferation such as actinic keratosis, arteriosclerosis, atherosclerosis, bursitis, cirrhosis, hepatitis, mixed connective tissue disease (MCTD), myelofibrosis, paroxysmal nocturnal hemoglobinuria, polycythemia vera, psoriasis, primary thrombocythemia, and cancers including adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; and an autoimmune/inflammatory disorder such as acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, autoimmune polyenodocrinopathy-candidiasis-ectodermal dystrophy (APECED), bronchitis, cholecystitis, contact dermatitis, Crohn's disease, atopic dermatitis, dermatomyositis, diabetes mellitus, emphysema, episodic lymphopenia with lymphocytotoxins, erythroblastosis fetalis, erythema nodosum, atrophic gastritis, glomerulonephritis, Goodpasture's syndrome, gout, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polymyositis, psoriasis, Reiter's syndrome, rheumatoid arthritis, scleroderma, Sjögren's syndrome, systemic anaphylaxis, systemic lupus erythematosus, systemic sclerosis, thrombocytopenic purpura, ulcerative colitis, uveitis, Werner syndrome, complications of cancer, hemodialysis, and extracorporeal circulation; viral, bacterial, fungal, parasitic, protozoal, and helminthic infections; and trauma. The polynucleotide sequences encoding MITP may be used in Southern or northern analysis, dot blot, or other membrane-based technologies; in PCR technologies; in dipstick, pin, and multiformat ELISA-like assays; and in microarrays utilizing fluids or tissues from patients to detect altered MITP expression. Such qualitative or quantitative methods are well known in the art.

In a particular aspect, the nucleotide sequences encoding MITP may be useful in assays that detect the presence of associated disorders, particularly those mentioned above. The nucleotide sequences encoding MITP may be labeled by standard methods and added to a fluid or tissue sample from a patient under conditions suitable for the formation of hybridization complexes. After a suitable incubation period, the sample is washed and the signal is quantified and compared with a standard value. If the amount of signal in the patient sample is significantly altered in comparison to a control sample then the presence of altered levels of nucleotide sequences encoding MITP in the sample indicates the presence of the associated disorder. Such assays may also be used to evaluate the efficacy of a particular therapeutic treatment regimen in animal studies, in clinical trials, or to monitor the treatment of an individual patient.

In order to provide a basis for the diagnosis of a disorder associated with expression of MITP, a normal or standard profile for expression is established. This may be accomplished by combining body fluids or cell extracts taken from normal subjects, either animal or human, with a sequence, or a fragment thereof, encoding MITP, under conditions suitable for hybridization or amplification. Standard hybridization may be quantified by comparing the values obtained from normal subjects with values from an experiment in which a known amount of a substantially purified polynucleotide is used. Standard values obtained in this manner may be compared with values obtained from samples from patients who are symptomatic for a disorder. Deviation from standard values is used to establish the presence of a disorder.

Once the presence of a disorder is established and a treatment protocol is initiated, hybridization assays may be repeated on a regular basis to determine if the level of expression in the patient begins to approximate that which is observed in the normal subject. The results obtained from successive assays may be used to show the efficacy of treatment over a period ranging from several days to months.

With respect to cancer, the presence of an abnormal amount of transcript (either under- or overexpressed) in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding MITP may involve the use of PCR. These oligomers may be chemically synthesized, generated enzymatically, or produced in vitro. Oligomers will preferably contain a fragment of a polynucleotide encoding MITP, or a fragment of a polynucleotide complementary to the polynucleotide encoding MITP, and will be employed under optimized conditions for identification of a specific gene or condition. Oligomers may also be employed under less stringent conditions for detection or quantification of closely related DNA or RNA sequences.

Methods which may also be used to quantify the expression of MITP include radiolabeling or biotinylating nucleotides, coamplification of a control nucleic acid, and interpolating results from standard curves. (See, e.g., Melby, P. C. et al. (1993) J. Immunol. Methods 159:235–244; Duplaa, C. et al. (1993) Anal. Biochem 212:229–236.) The speed of quantitation of multiple samples may be accelerated by running the assay in a high-throughput format where the oligomer of interest is presented in various dilutions and a spectrophotometric or calorimetric response gives rapid quantitation.

In further embodiments, oligonucleotides or longer fragments derived from any of the polynucleotide sequences described herein may be used as targets in a microarray. The microarray can be used to monitor the expression level of large numbers of genes simultaneously and to identify genetic variants, mutations, and polymorphisms. This information may be used to determine gene function, to understand the genetic basis of a disorder, to diagnose a disorder, and to develop and monitor the activities of therapeutic agents.

Microarrays may be prepared, used, and analyzed using methods known in the art. (See, e.g., Brennan, T. M. et al. (1995) U.S. Pat. No. 5,474,796; Schena, M. et al. (1996) Proc. Natl. Acad. Sci. USA 93:10614–10619; Baldeschweiler et al. (1995) PCT application WO95/251116; Shalon, D. et al. (1995) PCT application WO95/35505; Heller, R. A. et al. (1997) Proc. Natl. Acad. Sci. USA 94:2150–2155; and Heller, M. J. et al. (1997) U.S. Pat. No. 5,605,662.)

In another embodiment of the invention, nucleic acid sequences encoding MITP may be used to generate hybridization probes useful in mapping the naturally occurring genomic sequence. The sequences may be mapped to a particular chromosome, to a specific region of a chromosome, or to artificial chromosome constructions, e.g., human artificial chromosomes (HACs), yeast artificial chromosomes (YACs), bacterial artificial chromosomes (BACs), bacterial PI constructions, or single chromosome cDNA libraries. (See, e.g., Harrington, J. J. et al. (1997) Nat. Genet. 15:345–355; Price, C. M. (1993) Blood Rev. 7:127–134; and Trask, B. J. (1991) Trends Genet. 7:149–154.)

Fluorescent in situ hybridization (FISH) may be correlated with other physical chromosome mapping techniques and genetic map data. (See, e.g., Heinz-Ukich, et al. (1995) in Meyers, supra, pp. 965–968.) Examples of genetic map data can be found in various scientific journals or at the Online Mendelian Inheritance in Man (OMIM) World Wide Web site. Correlation between the location of the gene encoding MITP on a physical chromosomal map and a specific disorder, or a predisposition to a specific disorder, may help define the region of DNA associated with that disorder. The nucleotide sequences of the invention may be used to detect differences in gene sequences among normal, carrier, and affected individuals.

In situ hybridization of chromosomal preparations and physical mapping techniques, such as linkage analysis using established chromosomal markers, may be used for extending genetic maps. Often the placement of a gene on the chromosome of another mammalian species, such as mouse, may reveal associated markers even if the number or arm of a particular human chromosome is not known. New sequences can be assigned to chromosomal arms by physical mapping. This provides valuable information to investigators searching for disease genes using positional cloning or other gene discovery techniques. Once the disease or syndrome has been crudely localized by genetic linkage to a particular genomic region, e.g., ataxia-telangiectasia to 11q22–23, any sequences mapping to that area may represent associated or regulatory genes for further investigation. (See, e.g., Gatti, R. A. et al. (1988) Nature 336:577–580.) The nucleotide sequence of the subject invention may also be used to detect differences in the chromosomal location due to translocation, inversion, etc., among normal, carrier, or affected individuals.

In another embodiment of the invention, MITP, its catalytic or immunogenic fragments, or oligopeptides thereof can be used for screening libraries of compounds in any of a variety of drug screening techniques. The fragment employed in such screening may be free in solution, affixed to a solid support, borne on a cell surface, or located intracellularly. The formation of binding complexes between MITP and the agent being tested may be measured.

Another technique for drug screening provides for high throughput screening of compounds having suitable binding affinity to the protein of interest. (See, e.g., Geysen, et al. (1984) PCT application WO84/03564.) In this method, large numbers of different small test compounds are synthesized on a solid substrate. The test compounds are reacted with MITP, or fragments thereof, and washed. Bound MITP is then detected by methods well known in the art. Purified MITP can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding MITP specifically compete with a test compound for binding MITP. In this manner, antibodies can be used to detect the presence of any peptide which shares one or more antigenic determinants with MITP.

In additional embodiments, the nucleotide sequences which encode MITP may be used in any molecular biology techniques that have yet to be developed, provided the new techniques rely on properties of nucleotide sequences that are currently known, including, but not limited to, such properties as the triplet genetic code and specific base pair interactions.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

The disclosures of all patents, applications, and publications mentioned above and below, in particular U.S. Ser. No. 60/124,655, are hereby expressly incorporated by reference.

EXAMPLES

I. Construction of cDNA Libraries

RNA was purchased from Clontech or isolated from tissues described in Table 4. Some tissues were homogenized and lysed in guanidinium isothiocyanate, while others were homogenized and lysed in phenol or in a suitable mixture of denaturants, such as TRIZOL (Life Technologies), a monophasic solution of phenol and guanidine isothiocyanate. The resulting lysates were centrifuged over CsCl cushions or extracted with chloroform. RNA was precipitated from the lysates with either isopropanol or sodium acetate and ethanol, or by other routine methods.

Phenol extraction and precipitation of RNA were repeated as necessary to increase RNA purity. In some cases, RNA was treated with DNase. For most libraries, poly(A+) RNA was isolated using oligo d(T)-coupled paramagnetic particles (Promega), OLIGOTEX latex particles (QIAGEN, Chatsworth Calif.), or an OLIGOTEX mRNA purification kit (QIAGEN). Alternatively, RNA was isolated directly from tissue lysates using other RNA isolation kits, e.g., the POLY(A)PURE mRNA purification kit (Ambion, Austin Tex.).

In some cases, Stratagene was provided with RNA and constructed the corresponding cDNA libraries. Otherwise, cDNA was synthesized and cDNA libraries were constructed with the UNIZAP vector system (Stratagene) or SUPERSCRIPT plasmid system (Life Technologies), using the recommended procedures or similar methods known in the art. (See, e.g., Ausubel, 1997, supra, units 5.1–6.6.) Reverse transcription was initiated using oligo d(T) or random primers. Synthetic oligonucleotide adapters were ligated to double stranded cDNA, and the cDNA was digested with the appropriate restriction enzyme or enzymes. For most libraries, the cDNA was size-selected (300–1000 bp) using SEPHACRYL S1000, SEPHAROSE CL2B, or SEPHAROSE CL4B column chromatography (Amersham Pharmacia Biotech) or preparative agarose gel electrophoresis. cDNAs were ligated into compatible restriction enzyme sites of the polylinker of a suitable plasmid, e.g., PBLUESCRIPT plasmid (Stratagene), PSPORT1 plasmid (Life Technologies), pcDNA2.1 plasmid (Invitrogen, Carlsbad Calif.), or pINCY plasmid (Incyte Pharmaceuticals, Palo Alto Calif.). Recombinant plasmids were transformed into competent *E. coli* cells including XL1-Blue, XL1-BlueMRF, or SOLR from Stratagene or DH5α, DH10B, or ElectroMAX DH10B from Life Technologies.

II. Isolation of cDNA Clones

Plasmids were recovered from host cells by in vivo excision using the UNIZAP vector system (Stratagene) or by cell lysis. Plasmids were purified using at least one of the following: a Magic or WIZARD Minipreps DNA purification system (Promega); an AGTC Miniprep purification kit (Edge Biosystems, Gaithersburg Md.); and QIAWELL 8 Plasmid, QIAWELL 8 Plus Plasmid, QIAWELL 8 Ultra Plasmid purification systems or the R.E.A.L. PREP 96 plasmid purification kit from QIAGEN. Following precipitation, plasmids were resuspended in 0.1 ml of distilled water and stored, with or without lyophilization, at 4° C.

Alternatively, plasmid DNA was amplified from host cell lysates using direct link PCR in a high-throughput format (Rao, V. B. (1994) Anal. Biochem. 216:1–14). Host cell lysis and thermal cycling steps were carried out in a single reaction mixture. Samples were processed and stored in 384-well plates, and the concentration of amplified plasmid DNA was quantified fluorometrically using PICOGREEN dye (Molecular Probes, Eugene Oreg.) and a FLUOROSKAN II fluorescence scanner (Labsystems Oy, Helsinki, Finland).

III. Sequencing and Analysis cDNA sequencing reactions were processed using standard methods or high-throughput instrumentation such as the ABI CATALYST 800 (Perkin-Elmer) thermal cycler or the PTC-200 thermal cycler (MJ Research) in conjunction with the HYDRA microdispenser (Robbins Scientific) or the MICROLAB 2200 (Hamilton) liquid transfer system. cDNA sequencing reactions were prepared using reagents provided by Amersham Pharmacia Biotech or supplied in ABI sequencing kits such as the ABI PRISM BIGDYE Terminator cycle sequencing ready reaction kit (Perkin-Elmer). Electrophoretic separation of cDNA sequencing reactions and detection of labeled polynucleotides were carried out using the MEGABACE 1000 DNA sequencing system (Molecular Dynamics); the ABI PRISM 373 or 377 sequencing system (Perkin-Elmer) in conjunction with standard ABI protocols and base calling software; or other sequence analysis systems known in the art. Reading frames within the cDNA sequences were identified using standard methods (reviewed in Ausubel, 1997, supra, unit 7.7). Some of the cDNA sequences were selected for extension using the techniques disclosed in Example V.

The polynucleotide sequences derived from cDNA sequencing were assembled and analyzed using a combination of software programs which utilize algorithms well known to those skilled in the art. Table 5 summarizes the tools, programs, and algorithms used and provides applicable descriptions, references, and threshold parameters. The first column of Table 5 shows the tools, programs, and algorithms used, the second column provides brief descriptions thereof, the third column presents appropriate references, all of which are incorporated by reference herein in their entirety, and the fourth column presents, where applicable, the scores, probability values, and other parameters used to evaluate the strength of a match between two sequences (the higher the score, the greater the homology between two sequences). Sequences were analyzed using MACDNASIS PRO software (Hitachi Software Engineering, South San Francisco Calif.) and LASERGENE software (DNASTAR). Polynucleotide and polypeptide sequence alignments were generated using the default parameters specified by the clustal algorithm as incorporated into the MEGALIGN multisequence alignment program (DNASTAR), which also calculates the percent identity between aligned sequences.

The polynucleotide sequences were validated by removing vector, linker, and polyA sequences and by masking ambiguous bases, using algorithms and programs based on BLAST, dynamic programing, and dinucleotide nearest neighbor analysis. The sequences were then queried against a selection of public databases such as the GenBank primate, rodent, mammalian, vertebrate, and eukaryote databases, and BLOCKS, PRINTS, DOMO, PRODOM, and PFAM to acquire annotation using programs based on BLAST, FASTA, and BLIMPS. The sequences were assembled into full length polynucleotide sequences using programs based on Phred, Phrap, and Consed, and were screened for open reading frames using programs based on GeneMark, BLAST, and FASTA. The full length polynucleotide sequences were translated to derive the corresponding full length amino acid sequences, and these full length sequences were subsequently analyzed by querying against databases such as the GenBank databases (described above), SwissProt, BLOCKS, PRINTS, DOMO, PRODOM, Prosite, and Hidden Markov Model (HMM)-based protein family databases such as PFAM. HMM is a probabilistic approach which analyzes consensus primary structures of gene families. (See, e.g., Eddy, S. R. (1996) Curr. Opin. Struct. Biol. 6:361–365.)

The programs described above for the assembly and analysis of full length polynucleotide and amino acid sequences were also used to identify polynucleotide sequence fragments from SEQ ID NO:9–16. Fragments from about 20 to about 4000 nucleotides which are useful in hybridization and amplification technologies were described in The Invention section above.

IV. Northern Analysis

Northern analysis is a laboratory technique used to detect the presence of a transcript of a gene and involves the hybridization of a labeled nucleotide sequence to a membrane on which RNAs from a particular cell type or tissue have been bound. (See, e.g., Sambrook, supra, ch 7; Ausubel, 1995, supra, ch. 4 and 16.)

Analogous computer techniques applying BLAST were used to search for identical or related molecules in nucleotide databases such as GenBank or LIFESEQ (Incyte Pharmaceuticals). This analysis is much faster than multiple membrane-based hybridizations. In addition, the sensitivity of the computer search can be modified to determine whether any particular match is categorized as exact or similar. The basis of the search is the product score, which is defined as:

% sequence identity×% maximum BLAST score/100

The product score takes into account both the degree of similarity between two sequences and the length of the sequence match For example, with a product score of 40, the match will be exact within a 1% to 2% error, and, with a product score of 70, the match will be exact. Similar molecules are usually identified by selecting those which show product scores between 15 and 40, although lower scores may identify related molecules.

The results of northern analyses are reported as a percentage distribution of libraries in which the transcript encoding MITP occurred Analysis involved the categorization of cDNA libraries by organ/tissue and disease. The organ/tissue categories included cardiovascular, dermatologic, developmental, endocrine, gastrointestinal, hematopoietic/immune, musculoskeletal, nervous, reproductive, and urologic. The disease/condition categories included cancer, inflammation, trauma, cell proliferation, neurological, and pooled. For each category, the number of libraries expressing the sequence of interest was counted and divided by the total number of libraries across all categories. Percentage values of tissue-specific and disease- or condition-specific expression are reported in Table 3.

V. Extension of MITP Encoding Polynucleotides

The full length nucleic acid sequences of SEQ ID NO:9–16 were produced by extension of an appropriate fragment of the full length molecule using oligonucleotide primers designed from this fragment. One primer was synthesized to initiate 5' extension of the known fragment, and the other primer, to initiate 3' extension of the known fragment. The initial primers were designed using OLIGO 4.06 software (National Biosciences), or another appropriate program, to be about 22 to 30 nucleotides in length, to have a GC content of about 50% or more, and to anneal to the target sequence at temperatures of about 68° C. to about 72° C. Any stretch of nucleotides which would result in hairpin structures and primer-primer dimerizations was avoided.

Selected human cDNA libraries were used to extend the sequence. If more than one extension was necessary or desired, additional or nested sets of primers were designed.

High fidelity amplification was obtained by PCR using methods well known in the art. PCR was performed in 96-well plates using the PTC-200 thermal cycler (MJ Research, Inc.). The reaction mix contained DNA template, 200 nmol of each primer, reaction buffer containing $Mg^{2+}$, $(NH_4)_2SO_4$, and β-mercaptoethanol, Taq DNA polymerase (Amersham Pharmacia Biotech), ELONGASE enzyme (Life Technologies), and Pfu DNA polymerase (Stratagene), with the following parameters for primer pair PCI A and PCI B: Step 1: 94° C., 3 min; Step 2: 94° C., 15 sec; Step 3: 60° C., 1 min; Step 4: 68° C., 2 min; Step 5: Steps 2, 3, and 4 repeated 20 times; Step 6: 68° C., 5 min; Step 7: storage at 4° C. In the alternative, the parameters for primer pair T7 and SK+ were as follows: Step 1: 94° C., 3 min; Step 2: 94° C., 15 sec; Step 3: 57° C., 1 min; Step 4: 68° C., 2 min; Step 5: Steps 2, 3, and 4 repeated 20 times; Step 6: 68° C., 5 min; Step 7: storage at 4° C.

The concentration of DNA in each well was determined by dispensing 100 μl PICOGREEN quantitation reagent (0.25% (v/v) PICOGREEN; Molecular Probes, Eugene Oreg.) dissolved in 1×TE and 0.5 μl of undiluted PCR product into each well of an opaque fluorimeter plate (Corning Costar, Acton Mass.), allowing the DNA to bind to the reagent. The plate was scanned in a Fluoroskan II (Labsystems Oy, Helsinki, Finland) to measure the fluorescence of the sample and to quantify the concentration of DNA. A 5 μl to 10 μl aliquot of the reaction mixture was analyzed by electrophoresis on a 1% agarose mini-gel to determine which reactions were successful in extending the sequence.

The extended nucleotides were desalted and concentrated, transferred to 384-well plates, digested with CviJI cholera virus endonuclease (Molecular Biology Research, Madison Wis.), and sonicated or sheared prior to religation into pUC 18 vector (Amersham Pharmacia Biotech). For shotgun sequencing, the digested nucleotides were separated on low concentration (0.6 to 0.8%) agarose gels, fragments were excised, and agar digested with Agar ACE (Promega). Extended clones were religated using T4 ligase (New England Biolabs, Beverly Mass.) into pUC 18 vector (Amersham Pharmacia Biotech), treated with Pfu DNA polymerase (Stratagene) to fill-in restriction site overhangs, and transfected into competent *E. coli* cells. Transformed cells were selected on antibiotic-containing media, individual colonies were picked and cultured overnight at 37° C. in 384-well plates in LB/2× carb liquid media.

The cells were lysed, and DNA was amplified by PCR using Taq DNA polymerase (Amersham Pharmacia Biotech) and Pfu DNA polymerase (Stratagene) with the following parameters: Step 1: 94° C., 3 min; Step 2: 94° C., 15 sec;

Step 3: 60° C., 1 min; Step 4: 72° C., 2 min; Step 5: steps 2, 3, and 4 repeated 29 times; Step 6: 72° C., 5 min; Step 7: storage at 4° C. DNA was quantified by PICOGREEN reagent (Molecular Probes) as described above. Samples with low DNA recoveries were reamplified using the same conditions as described above. Samples were diluted with 20% dimethysulfoxide (1:2, v/v), and sequenced using DYENAMIC energy transfer sequencing primers and the DYENAMIC DIRECT kit (Amersham Pharmacia Biotech) or the ABI PRISM BIGDYE Terminator cycle sequencing ready reaction kit (Perkin-Elmer).

In like manner, the nucleotide sequences of SEQ ID NO:9–16 are used to obtain 5' regulatory sequences using the procedure above, oligonucleotides designed for such extension, and an appropriate genomic library.

VI. Labeling and Use of Individual Hybridization Probes

Hybridization probes derived from SEQ ID NO:9–16 are employed to screen cDNAs, genomic DNAs, or mRNAs. Although the labeling of oligonucleotides, consisting of about 20 base pairs, is specifically described, essentially the same procedure is used with larger nucleotide fragments. Oligonucleotides are designed using state-of-the-art software such as OLIGO 4.06 software (National Biosciences) and labeled by combining 50 pmol of each oligomer, 250 µCi of [γ-$^{32}$P] adenosine triphosphate (Amersham Pharmacia Biotech), and T4 polynucleotide kinase (DuPont NEN, Boston Mass.). The labeled oligonucleotides are substantially purified using a SEPHADEX G-25 superfine size exclusion dextran bead column (Amersham Pharmacia Biotech). An aliquot containing $10^7$ counts per minute of the labeled probe is used in a typical membrane-based hybridization analysis of human genomic DNA digested with one of the following endonucleases: Ase I, Bgl II, Eco RI, Pst I, Xba I, or Pvu II (DuPont NEN).

The DNA from each digest is fractionated on a 0.7% agarose gel and transferred to nylon membranes (Nytran Plus, Schleicher & Schuell, Durham N. H.). Hybridization is carried out for 16 hours at 40° C. To remove nonspecific signals, blots are sequentially washed at room temperature under conditions of up to, for example, 0.1× saline sodium citrate and 0.5% sodium dodecyl sulfate. Hybridization patterns are visualized using autoradiography or an alternative imaging means and compared.

VII. Microarrays

A chemical coupling procedure and an ink jet device can be used to synthesize array elements on the surface of a substrate. (See, e.g., Baldeschweiler, supra.) An array analogous to a dot or slot blot may also be used to arrange and link elements to the surface of a substrate using thermal, UV, chemical, or mechanical bonding procedures. A typical array may be produced by hand or using available methods and machines and contain any appropriate number of elements. After hybridization, nonhybridized probes are removed and a scanner used to determine the levels and patterns of fluorescence. The degree of complementarity and the relative abundance of each probe which hybridizes to an element on the microarray may be assessed through analysis of the scanned images.

Full-length cDNAs, Expressed Sequence Tags (ESTs), or fragments thereof may comprise the elements of the microarray. Fragments suitable for hybridization can be selected using software well known in the art such as LASERGENE software (DNASTAR). Full-length cDNAs, ESTs, or fragments thereof corresponding to one of the nucleotide sequences of the present invention, or selected at random from a cDNA library relevant to the present invention, are arranged on an appropriate substrate, e.g., a glass slide. The cDNA is fixed to the slide using, e.g., UV cross-linking followed by thermal and chemical treatments and subsequent drying. (See, e.g., Schena, M. et al. (1995) Science 270:467470; Shalon, D. et al. (1996) Genome Res. 6:639–645.) Fluorescent probes are prepared and used for hybridization to the elements on the substrate. The substrate is analyzed by procedures described above.

VIII. Complementary Polynucleotides

Sequences complementary to the MITP-encoding sequences, or any parts thereof, are used to detect, decrease, or inhibit expression of naturally occurring MITP. Although use of oligonucleotides comprising from about 15 to 30 base pairs is described, essentially the same procedure is used with smaller or with larger sequence fragments. Appropriate oligonucleotides are designed using OLIGO 4.06 software (National Biosciences) and the coding sequence of MITP. To inhibit transcription, a complementary oligonucleotide is designed from the most unique 5' sequence and used to prevent promoter binding to the coding sequence. To inhibit translation, a complementary oligonucleotide is designed to prevent ribosomal binding to the MITP-encoding transcript.

IX. Expression of MITP

Expression and purification of MITP is achieved using bacterial or virus-based expression systems. For expression of MITP in bacteria, cDNA is subcloned into an appropriate vector containing an antibiotic resistance gene and an inducible promoter that directs high levels of cDNA transcription. Examples of such promoters include, but are not limited to, the trp-lac (tac) hybrid promoter and the T5 or T7 bacteriophage promoter in conjunction with the lac operator regulatory element. Recombinant vectors are transformed into suitable bacterial hosts, e.g., BL21 (DE3). Antibiotic resistant bacteria express MITP upon induction with isopropyl beta-D-thiogalactopyranoside (IPTG). Expression of MITP in eukaryotic cells is achieved by infecting insect or mammalian cell lines with recombinant *Autographica californica* nuclear polyhedrosis virus (AcMNPV), commonly known as baculovirus. The nonessential polyhedrin gene of baculovirus is replaced with cDNA encoding MITP by either homologous recombination or bacterial-mediated transposition involving transfer plasmid intermediates. Viral infectivity is maintained and the strong polyhedrin promoter drives high levels of cDNA transcription. Recombinant baculovirus is used to infect *Spodoptera frugiperda* (Sf9) insect cells in most cases, or human hepatocytes, in some cases. Infection of the latter requires additional genetic modifications to baculovirus. (See Engelhard, E. K. et al. (1994) Proc. Natl. Acad. Sci. USA 91:3224–3227; Sandig, V. et al. (1996) Hum. Gene Ther. 7:1937–1945.)

In most expression systems, MITP is synthesized as a fusion protein with, e.g., glutathione S-transferase (GST) or a peptide epitope tag, such as FLAG or 6-His, permitting rapid, single-step, affinity-based purification of recombinant fusion protein from crude cell lysates. GST, a 26-kilodalton enzyme from *Schistosoma iaponicum*, enables the purification of fusion proteins on immobilized glutathione under conditions that maintain protein activity and antigenicity (Amersham Pharmacia Biotech). Following purification, the GST moiety can be proteolytically cleaved from MITP at specifically engineered sites. FLAG, an 8-amino acid peptide, enables immunoaffinity purification using commercially available monoclonal and polyclonal anti-FLAG antibodies (Eastman Kodak). 6-His, a stretch of six consecutive histidine residues, enables purification on metal-chelate resins (QIAGEN). Methods for protein expression and purification are discussed in Ausubel (1995, supra, ch. 10 and 16). Purified MITP obtained by these methods can be used directly in the following activity assay.

X. Demonstration of MITP Activity

MITP is demonstrated in three ways. In the first alternative, MITP activity is measured by the transfer of electrons from (and consequent oxidation of) NADH to cytochrome b5 when MITP is incubated together with NADH and cytochrome b5. The reaction is carried out in an optical cuvette containing aliquots of MITP together with 150 μM each of NADH and cytochrome b5 in 1 M Tris-acetate buffer, pH 8.1. The reaction is incubated at 21° C. and the oxidation of NADH is followed by the change in absorption at 340 nm using an ultraviolet spectrophotometer. The activity of MITP is proportional to the rate of change of absorption at 340 nm.

Alternatively, MITP activity is measured by the transfer of electrons from cytochrome c to an electron acceptor (KCN) in the presence of a reconstituted cytochrome c oxidase enzyme complex containing MITP in place of COX4. The reconstituted cytochrome c oxidase is incubated together with cytochrome c and KCN in a suitable buffer. The reaction is carried out in an optical cuvette and monitored by the change in absorption due to oxidation of cytochrome c using a spectrophotometer. Cytochrome c oxidase reconstituted in the absence of MITP is used as a negative control. The activity of MITP is proportional to the change in optical absorption measured.

In another alternative, MITP activity is measured in the reconstituted NADH-D complex by the catalysis of electron transfer from NADH to decylubiquinone (DB). The reaction contains 10 mg/mL NADH-D protein, 20 mM NADH in 50 mM tris-HCL buffer, pH 7.5, 50 mM NaCl, and 1 mM KCN. The reaction is started by addition of DB at 2 μM and followed by the change in absorbance at 340 nm due to the oxidation of NADH using an ultraviolet spectrophotometer. NADH-D complex reconstituted in the absence of NHETP-3 is compared as a negative control. The activity of MITP in the reconstituted NADH-D complex is proportional to the rate of change of absorbance at 340 nm.

XI. Functional Assays

MITP function is assessed by expressing the sequences encoding MITP at physiologically elevated levels in mammalian cell culture systems. cDNA is subcloned into a mammalian expression vector containing a strong promoter that drives high levels of cDNA expression. Vectors of choice include pCMV SPORT plasmid (Life Technologies) and pCR3.1 plasmid (Invitrogen), both of which contain the cytomegalovirus promoter. 5–10 μg of recombinant vector are transiently transfected into a human cell line, for example, an endothelial or hematopoietic cell line, using either liposome formulations or electroporation. 1–2 μg of an additional plasmid containing sequences encoding a marker protein are co-transfected. Expression of a marker protein provides a means to distinguish transfected cells from nontransfected cells and is a reliable predictor of cDNA expression from the recombinant vector. Marker proteins of choice include, e.g., Green Fluorescent Protein (GFP; Clontech), CD64, or a CD64-GFP fusion protein. Flow cytometry (FCM), an automated, laser optics-based technique, is used to identify transfected cells expressing GFP or CD64-GFP and to evaluate the apoptotic state of the cells and other cellular properties. FCM detects and quantifies the uptake of fluorescent molecules that diagnose events preceding or coincident with cell death. These events include changes in nuclear DNA content as measured by staining of DNA with propidium iodide; changes in cell size and granularity as measured by forward light scatter and 90 degree side light scatter; down-regulation of DNA synthesis as measured by decrease in bromodeoxyuridine uptake; alterations in expression of cell surface and intracellular proteins as measured by reactivity with specific antibodies; and alterations in plasma membrane composition as measured by the binding of fluorescein-conjugated Annexin V protein to the cell surface. Methods in flow cytometry are discussed in Ormerod, M. G. (1994) *Flow Cytometry*, Oxford, New York N.Y.

The influence of MITP on gene expression can be assessed using highly purified populations of cells transfected with sequences encoding MITP and either CD64 or CD64-GFP. CD64 and CD64-GFP are expressed on the surface of transfected cells and bind to conserved regions of human immunoglobulin G (IgG). Transfected cells are efficiently separated from nontransfected cells using magnetic beads coated with either human IgG or antibody against CD64 (DYNAL, Lake Success N.Y.). mRNA can be purified from the cells using methods well known by those of skill in the art. Expression of mRNA encoding MITP and other genes of interest can be analyzed by northern analysis or microarray techniques.

XII. Production of MITP Specific Antibodies

MITP substantially purified using polyacrylamide gel electrophoresis (PAGE; see, e.g., Harrington, M. G. (1990) Methods Enzymol. 182:488–495), or other purification techniques, is used to immunize rabbits and to produce antibodies using standard protocols.

Alternatively, the MITP amino acid sequence is analyzed using LASERGENE software (DNASTAR) to determine regions of high immunogenicity, and a corresponding oligopeptide is synthesized and used to raise antibodies by means known to those of skill in the art. Methods for selection of appropriate epitopes, such as those near the C-terminus or in hydrophilic regions are well described in the art. (See, e.g., Ausubel, 1995, supra, ch. 11.)

Typically, oligopeptides of about 15 residues in length are synthesized using an ABI 431A peptide synthesizer (Perkin-Elmer) using fmoc-chemistry and coupled to KLH (Sigma-Aldrich, St. Louis Mo.) by reaction with N-maleimidobenzoyl-N-hydroxysuccinimide ester (MBS) to increase immunogenicity. (See, e.g., Ausubel, 1995, supra.) Rabbits are immunized with the oligopeptide-KLH complex in complete Freund's adjuvant. Resulting antisera are tested for antipeptide and anti-MITP activity by, for example, binding the peptide or MITP to a substrate, blocking with 1% BSA, reacting with rabbit antisera, washing, and reacting with radio-iodinated goat anti-rabbit IgG.

XIII. Purification of Naturally Occurring MITP Using Specific Antibodies

Naturally occurring or recombinant MITP is substantially purified by immunoaffinity chromatography using antibodies specific for MITP. An immunoaffinity column is constructed by covalently coupling anti-MITP antibody to an activated chromatographic resin, such as CNBr-activated SEPHAROSE (Amersham Pharmacia Biotech). After the coupling, the resin is blocked and washed according to the manufacturer's instructions.

Media containing MITP are passed over the immunoaffinity column, and the column is washed under conditions that allow the preferential absorbance of MITP (e.g., high ionic strength buffers in the presence of detergent). The column is eluted under conditions that disrupt antibody/

MITP binding (e.g., a buffer of pH 2 to pH 3, or a high concentration of a chaotrope, such as urea or thiocyanate ion), and MITP is collected.

XIV. Identification of Molecules Which Interact with MITP

MITP, or biologically active fragments thereof, are labeled with $^{125}$I Bolton-Hunter reagent. (See, e.g., Bolton A. E. and W. M. Hunter (1973) Biochem. J. 133:529–539.) Candidate molecules previously arrayed in the wells of a multi-well plate are incubated with the labeled MITP, washed, and any wells with labeled MITP complex are assayed. Data obtained using different concentrations of MITP are used to calculate values for the number, affinity, and association of MITP with the candidate molecules.

Alternatively, molecules interacting with MITP are analyzed using the yeast two-hybrid system as described in Fields, S. and O. Song (1989, Nature 340:245–246), or using commercially available kits based on the two-hybrid system, such as the MATCHMAKER system (Clontech).

Various modifications and variations of the described methods and systems of the invention will be apparent to those skilled in the art without departing from the scope and spirit of the invention. Although the invention has been described in connection with certain embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

---

What is claimed is:

1. An isolated polynucleotide encoding a polypeptide comprising the amino acid sequence of SEQ ID NO:1.

2. The isolated polynucleotide of claim 1 comprising the polynucleotide sequence of SEQ ID NO:9.

3. A recombinant polynucleotide comprising a promoter sequence operably linked to the polynucleotide of claim 1.

4. A cell transformed with the recombinant polynucleotide of claim 3.

5. A method for producing the polypeptide encoded by the polynucleotide of claim 1, the method comprising:
  a) culturing a cell under conditions suitable for expression of the polypeptide, wherein said cell is transformed with a recombinant polynucleotide, and said recombinant polynucleotide comprises a promoter sequence operably linked to the polynucleotide of claim 1, and
  b) recovering the polypeptide so expressed.

* * * * *

UNITED STATES PATENT AND TRADEMARK OFFICE
CERTIFICATE OF CORRECTION

PATENT NO.         : 7,022,507 B1
APPLICATION NO.    : 09/525867
DATED              : April 4, 2006
INVENTOR(S)        : Henry Yue et al.

It is certified that error appears in the above-identified patent and that said Letters Patent is hereby corrected as shown below:

Insert the following Tables after column 46, and before the sequence listing:

Table 1

| Protein SEQ ID NO: | Nucleotide SEQ ID NO: | Clone ID | Library | Fragments |
|---|---|---|---|---|
| 1 | 9 | 1676225 | BLADNOT05 | 1510924F6 (LUNGNOT14), 1676225F6 (BLADNOT05), 1676225H1 (BLADNOT05), 1988463R6 (LUNGAST01), 3143066H1 (HNT2A2S07) |
| 2 | 10 | 2057235 | BEPINOT01 | 946212H1 (RATRNOT02), 989326H1 (LVENNOT03), 2057235H1 (BEPINOT01), 2057235R6 (BEPINOT01), 2059357T6 (OVARNOT03), 2885067H1 (SINJNOT02), 4331146H1 (KIDNNOT32) |
| 3 | 11 | 2186363 | PROSNOT26 | 029201R1 (SPLNFET01), 350269H1 (LVENNOT01), 982451T2 (TONGTUT01), 2186363H1 (PROSNOT26), 2186363X11C1 (PROSNOT26), 3011602H1 (MUSCNOT07), 4603644H1 (BRSTNOT07) |
| 4 | 12 | 3126833 | LUNGTUT12 | 1212133H1 (BRSTTUT01), 1503929F1 (BRAITUT07), 3126833H1 (LUNGTUT12) |
| 5 | 13 | 3446038 | FIBPNOT01 | 1695215H1 (COLNNOT23), 2103116T6 (BRAITUT02), 2778432F6 (OVARTUT03), 2969365F6 (HEAONOT02), 3446038H1 (FIBPNOT01), 4462290H1 (HEAADIT01), 5BHA01009F1 |
| 6 | 14 | 4113161 | UTRSTUT07 | 865350R1 (BRAITUT03), 1323856F1 (LPARNOT02), 1573915X11 (LNODNOT03), 1573915X13 (LNODNOT03), 1711996F6 (PROSNOT16), 2432241H1 (BRAVUNT02), 4113161H1 (UTRSTUT07) |
| 7 | 15 | 4408678 | OVARNOT13 | 4408537H1 (OVARNOT13), 4408678H1 (OVARNOT13) |
| 8 | 16 | 4942111 | BRAIFEN03 | 4942111F6 (BRAIFEN03), 4942111H1 (BRAIFEN03) |

UNITED STATES PATENT AND TRADEMARK OFFICE
CERTIFICATE OF CORRECTION

PATENT NO. : 7,022,507 B1
APPLICATION NO. : 09/525867
DATED : April 4, 2006
INVENTOR(S) : Henry Yue et al.

It is certified that error appears in the above-identified patent and that said Letters Patent is hereby corrected as shown below:

Table 2

| Protein SEQ ID NO: | Amino Acid Residues | Potential Phosphorylation Sites | Potential Glycosylation Sites | Signature Sequence | Identification | Analytical Methods |
|---|---|---|---|---|---|---|
| 1 | 213 | S78 S58 S57 S113 T127 | | Respiratory-chain NADH dehydrogenase 20 kD subunit: V91-E204 | PSST subunit of the NADH:ubiquinone oxidoreductase complex [Bos taurus].g599691 | Motifs BLAST BLOCKS Pfam |
| 2 | 303 | S115 T124 T214 S264 T75 S98 T145 | N277 | Mitochondrial carrier protein: A133-L187 | Mitochondrial carrier protein [Homo sapiens] g5815345 | Motifs BLAST BLOCKS Pfam |
| 3 | 294 | S164 T195 S229 T183 T231 Y284 | N27 N137 | | ABC1 protein [Arabidopsis thaliana] g3859609 | Motifs BLAST |
| 4 | 179 | S105 S170 | | Transmembrane domain: S20-L37 | Divalent cation tolerance protein [Homo sapiens] g4454995 | Motifs BLAST HMMER |
| 5 | 314 | S303 T92 T97 T109 T261 S279, S298 S303 | | Mitochondrial carrier protein: V33-V101, N108-K255, N256-L302 | Putative mitochondrial carrier protein [C. elegans] g3879122 | Motifs BLAST PRINTS ProfileScan Pfam |
| 6 | 544 | S126 S161 S209 T383 T427 T535 S539 T70 S76 T148 T318 T462 | | Protein intergenic region, ABC1 precursor, mitochondrial energy transfer: V149-Q158, V207-Q226, Q231-V251, V309-Q329 | ABC1 protein [C. elegans] g3859609 | Motifs BLOCKS |
| 7 | 128 | S26 S33 T39 Y43 | N122 | | Photosystem II 10 kD polypeptide [Oryza sativa] g1835731 | Motifs BLAST |
| 8 | 72 | T31 S69 | | | Ubiquinol-cytochrome c reductase [Solanum tuberosum] g633687 | Motifs BLAST |

Page 2 of 6

UNITED STATES PATENT AND TRADEMARK OFFICE
CERTIFICATE OF CORRECTION

PATENT NO.       : 7,022,507 B1
APPLICATION NO.  : 09/525867
DATED            : April 4, 2006
INVENTOR(S)      : Henry Yue et al.

It is certified that error appears in the above-identified patent and that said Letters Patent is hereby corrected as shown below:

Table 3

| Nucleotide SEQ ID NO: | Tissue Expression (Fraction of Total) | Disease or Condition (Fraction of Total) | Vector |
|---|---|---|---|
| 9 | Nervous (0.186) Reproductive (0.172) Cardiovascular (0.145) | Cell Proliferation (0.669) Inflammation/Immune (0.289) | pINCY |
| 10 | Reproductive (0.219) Gastrointestinal (0.190) Nervous (0.143) | Cell Proliferation (0.743) Inflammation/Immune (0.286) | PSPORT1 |
| 11 | Reproductive (0.256) Nervous (0.140) Gastrointestinal (0.128) | Cell Proliferation (0.686) Inflammation/Immune (0.314) | pINCY |
| 12 | Reproductive (0.259) Gastrointestinal (0.165) Nervous (0.147) | Cell Proliferation (0.697) Inflammation/Immune (0.295) | pINCY |
| 13 | Reproductive (0.250) Hematopoietic/Immune (0.188) Cardiovascular (0.125) | Cell Proliferation (0.563) Inflammation/Immune (0.437) | pINCY |
| 14 | Nervous (0.192) Gastrointestinal (0.154) Reproductive (0.154) | Cell Proliferation (0.557) Inflammation/Immune (0.365) | pINCY |
| 15 | Dermatologic (0.333) Cardiovascular (0.333) Reproductive (0.333) | Cell Proliferation (0.666) | pINCY |
| 16 | Nervous (1.000) | Cell Proliferation (1.000) | pINCY |

UNITED STATES PATENT AND TRADEMARK OFFICE
CERTIFICATE OF CORRECTION

PATENT NO. : 7,022,507 B1
APPLICATION NO. : 09/525867
DATED : April 4, 2006
INVENTOR(S) : Henry Yue et al.

It is certified that error appears in the above-identified patent and that said Letters Patent is hereby corrected as shown below:

Table 4

| Nucleotide SEQ ID NO: | Library | Library Comment |
|---|---|---|
| 9 | BLADNOT05 | Library was constructed using RNA isolated from bladder tissue removed from a 60-year-old Caucasian male during a radical cystectomy, prostatectomy, and vasectomy. Pathology for the associated tumor tissue indicated grade 3 transitional cell carcinoma. Carcinoma in-situ was identified in the dome and trigone. Patient history included tobacco use. |
| 10 | BEPINOT01 | Library was constructed using RNA isolated from a bronchial epithelium primary cell line derived from a 54-year-old Caucasian male. |
| 11 | PROSNOT26 | Library was constructed using RNA isolated from prostate tissue removed from a 65-year-old Caucasian male during a radical prostatectomy. Pathology for the associated tumor tissue indicated an adenocarcinoma. The patient presented with elevated prostate specific antigen (PSA). Family history included a malignant stomach neoplasm. |
| 12 | LUNGTUT12 | Library was constructed using RNA isolated from tumorous lung tissue removed from a 70-year-old Caucasian female during a lung lobectomy of the left upper lobe. Pathology indicated grade 3 (of 4) adenocarcinoma and vascular invasion. Patient history included tobacco abuse, depressive disorder, anxiety state, and skin cancer. Family history included cerebrovascular disease, congestive heart failure, colon cancer, depressive disorder, and primary liver. |
| 13 | PIBPNOT01 | Library was constructed using RNA isolated from fibroblasts of the prostate stroma removed from a male fetus, who died after 26 weeks' gestation. |

| Nucleotide SEQ ID NO: | Library | Library Comment |
|---|---|---|
| 14 | UTRSTUT07 | Library was constructed using RNA isolated from uterine tumor tissue removed from a 41-year-old Caucasian female during total abdominal hysterectomy with removal of an ovary and incidental appendectomy. Pathology indicated the endometrium was secretory phase, and the cervix showed microglandular hyperplasia. There were multiple (2 subserosal, 13 intramural, 1 submucosal) leiomyomas. Family history included atherosclerotic coronary artery disease, benign hypertension, depression, and type II diabetes. |
| 15 | OVARNOT13 | Library was constructed using RNA isolated from left ovary tissue removed from a 47-year-old Caucasian female during a vaginal hysterectomywith bilateral salpingo-oophorectomy, and dilation and curettage. Pathology for the associated tumor tissue indicated a single intramural leiomyoma. The endometrium was in the secretory phase. The patient presented with menorrhagia. Patient history included hyperlipidemia and benign hypertension. Family history included colon cancer, benign hypertension, atherosclerotic coronary artery disease, and breast cancer. |
| 16 | BRAIFEN03 | This normalized fetal brain tissue library was constructed from 3.26 million independent clones from the BRAIFET02 library. Starting RNA was made from brain tissue removed from a Caucasian male fetus with a hypoplastic left heart stillborn after 23 weeks' gestation. The library was normalized in two rounds. (with 48 hour reannealing hybridizations) using conditions adapted from Soares et al. (Proc. Natl. Acad. Sci. USA (1994) 91:9928) and Bonaldo et al. (Genome Research (1996) 6:791). |

UNITED STATES PATENT AND TRADEMARK OFFICE
CERTIFICATE OF CORRECTION

PATENT NO. : 7,022,507 B1
APPLICATION NO. : 09/525867
DATED : April 4, 2006
INVENTOR(S) : Henry Yue et al.

It is certified that error appears in the above-identified patent and that said Letters Patent is hereby corrected as shown below:

Table 5

| Program | Description | Reference | Parameter Threshold |
|---|---|---|---|
| ABI FACTURA | A program that removes vector sequences and masks ambiguous bases in nucleic acid sequences. | Perkin-Elmer Applied Biosystems, Foster City, CA. | |
| ABI/PARACEL FDF | A Fast Data Finder useful in comparing and annotating amino acid or nucleic acid sequences. | Perkin-Elmer Applied Biosystems, Foster City, CA; Paracel Inc., Pasadena, CA. | Mismatch <50% |
| ABI AutoAssembler | A program that assembles nucleic acid sequences. | Perkin-Elmer Applied Biosystems, Foster City, CA. | |
| BLAST | A Basic Local Alignment Search Tool useful in sequence similarity search for amino acid and nucleic acid sequences. BLAST includes five functions: blastp, blastn, blastx, tblastn, and tblastx. | Altschul, S.F. et al. (1990) J. Mol. Biol. 215:403-410; Altschul, S.F. et al. (1997) Nucleic Acids Res. 25: 3389-3402. | ESTs: Probability value= 1.0E-8 or less. Full Length sequences: Probability value= 1.0E-10 or less |
| FASTA | A Pearson and Lipman algorithm that searches for similarity between a query sequence and a group of sequences of the same type. FASTA comprises at least five functions: fasta, tfasta, fastx, tfastx, and ssearch. | Pearson, W.R. and D.J. Lipman (1988) Proc. Natl. Acad. Sci. 85:2444-2448; Pearson, W.R. (1990) Methods Enzymol. 183: 63-98; and Smith, T.F. and M.S. Waterman (1981) Adv. Appl. Math. 2:482-489. | ESTs: fasta E value=1.06E-6 Assembled ESTs: fasta Identity= 95% or greater and Match length=200 bases or greater; fastx E value=1.0E-8 or less Full Length sequences: fastx score=100 or greater |
| BLIMPS | A BLocks IMProved Searcher that matches a sequence against those in BLOCKS, PRINTS, DOMO, PRODOM, and PFAM databases to search for gene families, sequence homology, and structural fingerprint regions. | Henikoff, S and J.G. Henikoff, Nucl. Acid Res., 19:6565-72, 1991. J.G. Henikoff and S. Henikoff (1996) Methods Enzymol. 266:88-105; and Attwood, T.K. et al. (1997) J. Chem. Inf. Comput. Sci. 37: 417-424. | Score=1000 or greater; Ratio of Score/Strength = 0.75 or larger; and, if applicable, Probability value= 1.0E-3 or less |
| HMMER | An algorithm for searching a query sequence against hidden Markov model (HMM)-based databases of protein family consensus sequences, such as PFAM. | Krogh, A. et al. (1994) J. Mol. Biol., 235:1501-1531; Sonnhammer, E.L.L. et al. (1988) Nucleic Acids Res. 26:320-322. | Score=10-50 bits for PFAM hits, depending on individual protein families |

UNITED STATES PATENT AND TRADEMARK OFFICE
CERTIFICATE OF CORRECTION

PATENT NO. : 7,022,507 B1
APPLICATION NO. : 09/525867
DATED : April 4, 2006
INVENTOR(S) : Henry Yue et al.

It is certified that error appears in the above-identified patent and that said Letters Patent is hereby corrected as shown below:

Table 5 (cont.)

| Program | Description | Reference | Parameter Threshold |
|---|---|---|---|
| ProfileScan | An algorithm that searches for structural and sequence motifs in protein sequences that match sequence patterns defined in Prosite. | Gribskov, M. et al. (1988) CABIOS 4:61-66; Gribskov, et al. (1989) Methods Enzymol. 183:146-159; Bairoch, A. et al. (1997) Nucleic Acids Res. 25: 217-221. | Normalized quality score≥GCG-specified "HIGH" value for that particular Prosite motif. Generally, score=1.4-2.1. |
| Phred | A base-calling algorithm that examines automated sequencer traces with high sensitivity and probability. | Ewing, B. et al. (1998) Genome Res. 8:175-185; Ewing, B. and P. Green (1998) Genome Res. 8:186-194. | |
| Phrap | A Phils Revised Assembly Program Including SWAT and CrossMatch, programs based on efficient implementation of the Smith-Waterman algorithm, useful in searching sequence homology and assembling DNA sequences. | Smith, T.F. and M. S. Waterman (1981) Adv. Appl. Math. 2:482-489; Smith, T.F. and M. S. Waterman (1981) J. Mol. Biol. 147:195-197; and Green, P., University of Washington, Seattle, WA. | Score= 120 or greater; Match length= 56 or greater |
| Consed | A graphical tool for viewing and editing Phrap assemblies | Gordon, D. et al. (1998) Genome Res. 8:195-202. | |
| SPScan | A weight matrix analysis program that scans protein sequences for the presence of secretory signal peptides. | Nielson, H. et al. (1997) Protein Engineering 10:1-6; Claverie, J.M. and S. Audic (1997) CABIOS 12: 431-439. | Score=3.5 or greater |
| Motifs | A program that searches amino acid sequences for patterns that matched those defined in Prosite. | Bairoch et al., supra; Wisconsin Package Program Manual, version 9, page M51-59, Genetics Computer Group, Madison, WI. | |

Signed and Sealed this

Thirty-first Day of July, 2007

JON W. DUDAS
*Director of the United States Patent and Trademark Office*

SEQUENCE LISTING

```
<160> NUMBER OF SEQ ID NOS: 16

<210> SEQ ID NO 1
<211> LENGTH: 213
<212> TYPE: PRT
<213> ORGANISM: Homo sapiens
<220> FEATURE:
<221> NAME/KEY: misc_feature
<223> OTHER INFORMATION: Incyte ID No: 1676225CD1

<400> SEQUENCE: 1

Met Ala Val Leu Ser Ala Pro Gly Leu Arg Gly Phe Arg Ile Leu
 1               5                  10                  15

Gly Leu Arg Ser Ser Val Gly Pro Ala Val Gln Ala Arg Gly Val
                20                  25                  30

His Gln Ser Val Ala Thr Asp Gly Pro Ser Ser Thr Gln Pro Ala
                35                  40                  45

Leu Pro Lys Ala Arg Ala Val Ala Pro Lys Pro Ser Ser Arg Gly
                50                  55                  60

Glu Tyr Val Val Ala Lys Leu Asp Asp Leu Val Asn Trp Ala Arg
                65                  70                  75

Arg Ser Ser Leu Trp Pro Met Thr Phe Gly Leu Ala Cys Cys Ala
                80                  85                  90

Val Glu Met Met His Met Ala Ala Pro Arg Tyr Asp Met Asp Arg
                95                  100                 105

Phe Gly Val Val Phe Arg Ala Ser Pro Arg Gln Ser Asp Val Met
                110                 115                 120

Ile Val Ala Gly Thr Leu Thr Asn Lys Met Ala Pro Ala Leu Arg
                125                 130                 135

Lys Val Tyr Asp Gln Met Pro Glu Pro Arg Tyr Val Val Ser Met
                140                 145                 150

Gly Ser Cys Ala Asn Gly Gly Gly Tyr Tyr His Tyr Ser Tyr Ser
                155                 160                 165

Val Val Arg Gly Cys Asp Arg Ile Val Pro Val Asp Ile Tyr Ile
                170                 175                 180

Pro Gly Cys Pro Pro Thr Ala Glu Ala Leu Leu Tyr Gly Ile Leu
                185                 190                 195

Gln Leu Gln Arg Lys Ile Lys Arg Glu Arg Leu Gln Ile Trp
                200                 205                 210

Tyr Arg Arg
```

-continued

```
<210> SEQ ID NO 2
<211> LENGTH: 303
<212> TYPE: PRT
<213> ORGANISM: Homo sapiens
<220> FEATURE:
<221> NAME/KEY: misc_feature
<223> OTHER INFORMATION: Incyte ID No: 2057235CD1

<400> SEQUENCE: 2

Met Ala Asp Ala Ala Ser Gln Val Leu Leu Gly Ser Gly Leu Thr
  1               5                  10                  15

Ile Leu Ser Gln Pro Leu Met Tyr Val Lys Val Leu Ile Gln Val
                 20                  25                  30

Gly Tyr Glu Pro Leu Pro Pro Thr Ile Gly Arg Asn Ile Phe Gly
                 35                  40                  45

Arg Gln Val Cys Gln Leu Pro Gly Leu Phe Ser Tyr Ala Gln His
                 50                  55                  60

Ile Ala Ser Ile Asp Gly Arg Gly Leu Phe Thr Gly Leu Thr
                 65                  70                  75

Pro Arg Leu Cys Ser Gly Val Leu Gly Thr Val Val His Gly Lys
                 80                  85                  90

Val Leu Gln His Tyr Gln Glu Ser Asp Lys Gly Glu Leu Gly
                 95                 100                 105

Pro Gly Asn Val Gln Lys Glu Val Ser Ser Phe Asp His Val
                110                 115                 120

Ile Lys Glu Thr Thr Arg Glu Met Ile Ala Arg Ser Ala Ala Thr
                125                 130                 135

Leu Ile Thr His Pro Phe His Val Ile Thr Leu Arg Ser Met Val
                140                 145                 150

Gln Phe Ile Gly Arg Glu Ser Lys Tyr Cys Gly Leu Cys Asp Ser
                155                 160                 165

Ile Ile Thr Ile Tyr Arg Glu Glu Gly Ile Leu Gly Phe Phe Ala
                170                 175                 180

Gly Leu Val Pro Arg Leu Leu Gly Asp Ile Leu Ser Leu Trp Leu
                185                 190                 195

Cys Asn Ser Leu Ala Tyr Leu Val Asn Thr Tyr Ala Leu Asp Ser
                200                 205                 210

Gly Val Ser Thr Met Asn Glu Met Lys Ser Tyr Ser Gln Ala Val
                215                 220                 225

Thr Gly Phe Phe Ala Ser Met Leu Thr Tyr Pro Phe Val Leu Val
                230                 235                 240

Ser Asn Leu Met Ala Val Asn Asn Cys Gly Leu Ala Gly Gly Cys
                245                 250                 255

Pro Pro Tyr Ser Pro Ile Tyr Thr Ser Trp Ile Asp Cys Trp Cys
                260                 265                 270

Met Leu Gln Lys Glu Gly Asn Met Ser Arg Gly Asn Ser Leu Phe
                275                 280                 285

Phe Arg Lys Val Ala Phe Gly Lys Thr Tyr Cys Cys Asp Leu Lys
                290                 295                 300

Met Leu Ile

<210> SEQ ID NO 3
<211> LENGTH: 294
<212> TYPE: PRT
<213> ORGANISM: Homo sapiens
<220> FEATURE:
```

```
<221> NAME/KEY: misc_feature
<223> OTHER INFORMATION: Incyte ID No: 2186363CD1

<400> SEQUENCE: 3
```

| | | | | | | | | | | | | | | |
|---|---|---|---|---|---|---|---|---|---|---|---|---|---|---|
| Met | Pro | Leu | Lys | Gln | Met | Met | Tyr | Pro | Gly | Val | Ala | Gln | Ser | Ile |
| 1 | | | | 5 | | | | | 10 | | | | | 15 |
| Asn | Ser | Asp | Val | Asn | Asn | Leu | Met | Ala | Val | Leu | Asn | Met | Ser | Asn |
| | | | | 20 | | | | | 25 | | | | | 30 |
| Met | Leu | Pro | Glu | Gly | Leu | Phe | Pro | Glu | His | Leu | Ile | Asp | Val | Leu |
| | | | | 35 | | | | | 40 | | | | | 45 |
| Arg | Arg | Glu | Leu | Ala | Leu | Glu | Cys | Asp | Tyr | Gln | Arg | Glu | Ala | Ala |
| | | | | 50 | | | | | 55 | | | | | 60 |
| Cys | Ala | Arg | Lys | Phe | Arg | Asp | Leu | Leu | Lys | Gly | His | Pro | Phe | Phe |
| 65 | | | | | 70 | | | | | 75 | | | | |
| Tyr | Val | Pro | Glu | Ile | Val | Asp | Glu | Leu | Cys | Ser | Pro | His | Val | Leu |
| | | | | 80 | | | | | 85 | | | | | 90 |
| Thr | Thr | Glu | Leu | Val | Ser | Gly | Phe | Pro | Leu | Asp | Gln | Ala | Glu | Gly |
| | | | | 95 | | | | | 100 | | | | | 105 |
| Leu | Ser | Gln | Glu | Ile | Arg | Asn | Glu | Ile | Cys | Tyr | Asn | Ile | Leu | Val |
| | | | | 110 | | | | | 115 | | | | | 120 |
| Leu | Cys | Leu | Arg | Glu | Leu | Phe | Glu | Phe | His | Phe | Met | Gln | Thr | Asp |
| | | | | 125 | | | | | 130 | | | | | 135 |
| Pro | Asn | Trp | Ser | Asn | Phe | Phe | Tyr | Asp | Pro | Gln | Gln | His | Lys | Val |
| | | | | 140 | | | | | 145 | | | | | 150 |
| Ala | Leu | Leu | Asp | Phe | Gly | Ala | Thr | Arg | Glu | Tyr | Asp | Arg | Ser | Phe |
| | | | | 155 | | | | | 160 | | | | | 165 |
| Thr | Asp | Leu | Tyr | Ile | Gln | Ile | Ile | Arg | Ala | Ala | Ala | Asp | Arg | Asp |
| | | | | 170 | | | | | 175 | | | | | 180 |
| Arg | Glu | Thr | Val | Arg | Ala | Lys | Ser | Ile | Glu | Met | Lys | Phe | Leu | Thr |
| | | | | 185 | | | | | 190 | | | | | 195 |
| Gly | Tyr | Glu | Val | Lys | Val | Met | Glu | Asp | Ala | His | Leu | Asp | Ala | Ile |
| | | | | 200 | | | | | 205 | | | | | 210 |
| Leu | Ile | Leu | Gly | Glu | Ala | Phe | Ala | Ser | Asp | Glu | Pro | Phe | Asp | Phe |
| | | | | 215 | | | | | 220 | | | | | 225 |
| Gly | Thr | Gln | Ser | Thr | Thr | Glu | Lys | Ile | His | Asn | Leu | Ile | Pro | Val |
| | | | | 230 | | | | | 235 | | | | | 240 |
| Met | Leu | Arg | His | Arg | Leu | Val | Pro | Pro | Glu | Glu | Thr | Tyr | Ser |
| | | | | 245 | | | | | 250 | | | | | 255 |
| Leu | His | Arg | Lys | Met | Gly | Gly | Ser | Phe | Leu | Ile | Cys | Ser | Lys | Leu |
| | | | | 260 | | | | | 265 | | | | | 270 |
| Lys | Ala | Arg | Phe | Pro | Cys | Lys | Ala | Met | Phe | Glu | Glu | Ala | Tyr | Ser |
| | | | | 275 | | | | | 280 | | | | | 285 |
| Asn | Tyr | Cys | Lys | Arg | Gln | Ala | Gln | Gln | | | | | | |
| | | | | 290 | | | | | | | | | | |

```
<210> SEQ ID NO 4
<211> LENGTH: 179
<212> TYPE: PRT
<213> ORGANISM: Homo sapiens
<220> FEATURE:
<221> NAME/KEY: misc_feature
<223> OTHER INFORMATION: Incyte ID No: 3126833CD1

<400> SEQUENCE: 4
```

| | | | | | | | | | | | | | | |
|---|---|---|---|---|---|---|---|---|---|---|---|---|---|---|
| Met | Ser | Gly | Gly | Arg | Ala | Pro | Ala | Val | Leu | Leu | Gly | Gly | Val | Ala |
| 1 | | | | 5 | | | | | 10 | | | | | 15 |

-continued

```
Ser Leu Leu Leu Ser Phe Val Trp Met Pro Ala Leu Leu Pro Val
             20                  25                  30

Ala Ser Arg Leu Leu Leu Pro Arg Val Leu Leu Thr Met Ala
         35                  40                  45

Ser Gly Ser Pro Pro Thr Gln Pro Ser Pro Ala Ser Asp Ser Gly
             50                  55                  60

Ser Gly Tyr Val Pro Gly Ser Val Ser Ala Ala Phe Val Thr Cys
             65                  70                  75

Pro Asn Glu Lys Val Ala Lys Glu Ile Ala Arg Ala Val Val Glu
             80                  85                  90

Lys Arg Leu Ala Ala Cys Val Asn Leu Ile Pro Gln Ile Thr Ser
             95                 100                 105

Ile Tyr Glu Trp Lys Gly Lys Ile Glu Glu Asp Ser Glu Val Leu
            110                 115                 120

Met Met Ile Lys Thr Gln Ser Ser Leu Val Pro Ala Leu Thr Asp
            125                 130                 135

Phe Val Arg Ser Val His Pro Tyr Glu Val Ala Glu Val Ile Ala
            140                 145                 150

Leu Pro Val Glu Gln Gly Asn Phe Pro Tyr Leu Gln Trp Val Arg
            155                 160                 165

Gln Val Thr Glu Ser Val Ser Asp Ser Ile Thr Val Leu Pro
            170                 175
```

<210> SEQ ID NO 5
<211> LENGTH: 314
<212> TYPE: PRT
<213> ORGANISM: Homo sapiens
<220> FEATURE:
<221> NAME/KEY: misc_feature
<223> OTHER INFORMATION: Incyte ID No: 3446038CD1

<400> SEQUENCE: 5

```
Met Glu Asp Lys Arg Asn Ile Gln Ile Ile Glu Trp Glu His Leu
 1               5                  10                  15

Asp Lys Lys Lys Phe Tyr Val Phe Gly Val Ala Met Thr Met Met
             20                  25                  30

Ile Arg Val Ser Val Tyr Pro Phe Thr Leu Ile Arg Thr Arg Leu
         35                  40                  45

Gln Val Gln Lys Gly Lys Ser Leu Tyr His Gly Thr Phe Asp Ala
             50                  55                  60

Phe Ile Lys Ile Leu Arg Ala Asp Gly Ile Thr Gly Leu Tyr Arg
             65                  70                  75

Gly Phe Leu Val Asn Thr Phe Thr Leu Ile Ser Gly Gln Cys Tyr
             80                  85                  90

Val Thr Thr Tyr Glu Leu Thr Arg Lys Phe Val Ala Asp Tyr Ser
             95                 100                 105

Gln Ser Asn Thr Val Lys Ser Leu Val Ala Gly Gly Ser Ala Ser
            110                 115                 120

Leu Val Ala Gln Ser Ile Thr Val Pro Ile Asp Val Val Ser Gln
            125                 130                 135

His Leu Met Met Gln Arg Lys Gly Glu Lys Met Gly Arg Phe Gln
            140                 145                 150

Val Arg Gly Asn Ser Glu Gly Gln Gly Val Val Ala Phe Gly Gln
            155                 160                 165

Thr Lys Asp Ile Ile Arg Gln Ile Leu Gln Ala Asp Gly Leu Arg
            170                 175                 180
```

-continued

```
Gly Phe Tyr Arg Gly Tyr Val Ala Ser Leu Leu Thr Tyr Ile Pro
            185                 190                 195

Asn Ser Ala Val Trp Trp Pro Phe Tyr His Phe Tyr Ala Glu Gln
            200                 205                 210

Leu Ser Tyr Leu Cys Pro Lys Glu Cys Pro His Ile Val Phe Gln
            215                 220                 225

Ala Val Ser Gly Pro Leu Ala Ala Thr Ala Ser Ile Leu Thr
            230                 235                 240

Asn Pro Met Asp Val Ile Arg Thr Arg Val Gln Val Glu Gly Lys
            245                 250                 255

Asn Ser Ile Ile Leu Thr Phe Arg Gln Leu Met Ala Glu Gly
            260                 265                 270

Pro Trp Gly Leu Met Lys Gly Leu Ser Ala Arg Ile Ile Ser Ala
            275                 280                 285

Thr Pro Ser Thr Ile Val Ile Val Val Gly Tyr Glu Ser Leu Lys
            290                 295                 300

Lys Leu Ser Leu Arg Pro Glu Leu Val Asp Ser Arg His Trp
            305                 310
```

<210> SEQ ID NO 6
<211> LENGTH: 544
<212> TYPE: PRT
<213> ORGANISM: Homo sapiens
<220> FEATURE:
<221> NAME/KEY: misc_feature
<223> OTHER INFORMATION: Incyte ID No: 4113161CD1

<400> SEQUENCE: 6

```
Met Trp Leu Lys Val Gly Gly Leu Leu Arg Gly Thr Gly Gly Gln
 1               5                  10                  15

Leu Gly Gln Thr Val Gly Trp Pro Cys Gly Ala Leu Gly Pro Gly
            20                  25                  30

Pro His Arg Trp Gly Pro Cys Gly Gly Ser Trp Ala Gln Lys Phe
            35                  40                  45

Tyr Gln Asp Gly Pro Gly Arg Gly Leu Gly Glu Glu Asp Ile Arg
            50                  55                  60

Arg Ala Arg Glu Ala Arg Pro Arg Lys Thr Pro Arg Pro Gln Leu
            65                  70                  75

Ser Asp Arg Ser Arg Glu Arg Lys Val Pro Ala Ser Arg Ile Ser
            80                  85                  90

Arg Leu Ala Asn Phe Gly Gly Leu Ala Val Gly Leu Gly Leu Gly
            95                  100                 105

Val Leu Ala Glu Met Ala Lys Lys Ser Met Pro Gly Gly Arg Leu
            110                 115                 120

Gln Ser Glu Gly Gly Ser Gly Leu Asp Ser Ser Pro Phe Leu Ser
            125                 130                 135

Glu Ala Asn Ala Glu Arg Ile Val Gln Thr Leu Cys Thr Val Arg
            140                 145                 150

Gly Ala Ala Leu Lys Val Gly Gln Met Leu Ser Ile Gln Asp Asn
            155                 160                 165

Ser Phe Ile Ser Pro Gln Leu Gln His Ile Phe Glu Arg Val Arg
            170                 175                 180

Gln Ser Ala Asp Phe Met Pro Arg Trp Gln Met Leu Arg Val Leu
            185                 190                 195

Glu Glu Glu Leu Gly Arg Asp Trp Gln Ala Lys Val Ala Ser Leu
```

```
                     200                 205                 210
Glu Glu Val Pro Phe Ala Ala Ala Ser Ile Gly Gln Val His Gln
                215                 220                 225
Gly Leu Leu Arg Asp Gly Thr Glu Val Ala Val Lys Ile Gln Tyr
                230                 235                 240
Pro Gly Ile Ala Gln Ser Ile Gln Ser Asp Val Gln Asn Leu Leu
                245                 250                 255
Ala Val Leu Lys Met Ser Ala Ala Leu Pro Ala Gly Leu Phe Ala
                260                 265                 270
Glu Gln Ser Leu Gln Ala Leu Gln Gln Glu Leu Ala Trp Glu Cys
                275                 280                 285
Asp Tyr Arg Arg Glu Ala Ala Cys Ala Gln Asn Phe Arg Gln Leu
                290                 295                 300
Leu Ala Asn Asp Pro Phe Phe Arg Val Pro Ala Val Val Lys Glu
                305                 310                 315
Leu Cys Thr Thr Arg Val Leu Gly Met Glu Leu Ala Gly Gly Val
                320                 325                 330
Pro Leu Asp Gln Cys Gln Gly Leu Ser Gln Asp Leu Arg Asn Gln
                335                 340                 345
Ile Cys Phe Gln Leu Leu Thr Leu Cys Leu Arg Glu Leu Phe Glu
                350                 355                 360
Phe Arg Phe Met Gln Thr Asp Pro Asn Trp Ala Asn Phe Leu Tyr
                365                 370                 375
Asp Ala Ser Ser His Gln Val Thr Leu Leu Asp Phe Gly Ala Ser
                380                 385                 390
Arg Glu Phe Gly Thr Glu Phe Thr Asp His Tyr Ile Glu Val Val
                395                 400                 405
Lys Ala Ala Ala Asp Gly Asp Arg Asp Cys Val Leu Gln Lys Ser
                410                 415                 420
Arg Asp Leu Lys Phe Leu Thr Gly Phe Glu Thr Lys Ala Phe Ser
                425                 430                 435
Asp Ala His Val Glu Ala Val Met Ile Leu Gly Glu Pro Phe Ala
                440                 445                 450
Thr Gln Gly Pro Tyr Asp Phe Gly Ser Gly Glu Thr Ala Arg Arg
                455                 460                 465
Ile Gln Asp Leu Ile Pro Val Leu Leu Arg His Arg Leu Cys Pro
                470                 475                 480
Pro Pro Glu Glu Thr Tyr Ala Leu His Arg Lys Leu Ala Gly Ala
                485                 490                 495
Phe Leu Ala Cys Ala His Leu Arg Ala His Ile Ala Cys Arg Asp
                500                 505                 510
Leu Phe Gln Asp Thr Tyr His Arg Tyr Trp Ala Ser Arg Gln Pro
                515                 520                 525
Asp Ala Ala Thr Ala Gly Ser Leu Pro Thr Lys Gly Asp Ser Trp
                530                 535                 540
Val Asp Pro Ser

<210> SEQ ID NO 7
<211> LENGTH: 128
<212> TYPE: PRT
<213> ORGANISM: Homo sapiens
<220> FEATURE:
<221> NAME/KEY: misc_feature
<223> OTHER INFORMATION: Incyte ID No: 4408678CD1
```

-continued

<400> SEQUENCE: 7

Met Ala Ala Ser Met Ile Ser Ser Ala Leu Ala Val Ala Pro
1               5                   10                  15

Gln Gly Leu Pro Pro Leu Gly Arg Arg Ala Ser Ser Phe Ala Val
            20                  25                  30

Val Cys Ser Lys Lys Lys Ile Lys Thr Asp Lys Pro Tyr Gly Ile
        35                  40                  45

Gly Gly Gly Leu Thr Val Asp Val Asp Ala Asn Gly Arg Lys Gly
            50                  55                  60

Lys Gly Lys Gly Val Tyr Gln Phe Val Asp Lys Tyr Gly Ala Asn
65                  70                  75

Val Asp Gly Tyr Ser Pro Ile Tyr Asn Glu Asp Asp Trp Ser Pro
                80                  85                  90

Thr Gly Asp Val Tyr Val Gly Gly Thr Thr Gly Leu Leu Ile Trp
            95                  100                 105

Ala Val Thr Leu Ala Gly Ile Leu Gly Gly Ala Leu Leu Val
            110                 115                 120

Tyr Asn Thr Ser Ala Leu Ser Gly
                125

<210> SEQ ID NO 8
<211> LENGTH: 72
<212> TYPE: PRT
<213> ORGANISM: Homo sapiens
<220> FEATURE:
<221> NAME/KEY: misc_feature
<223> OTHER INFORMATION: Incyte ID No: 4942111CD1

<400> SEQUENCE: 8

Met Gly Lys Thr Pro Val Arg Met Lys Ala Val Val Tyr Ala Leu
1               5                   10                  15

Ser Pro Phe Gln Gln Lys Val Met Pro Gly Leu Trp Lys Asp Ile
            20                  25                  30

Thr Thr Lys Ile His His Lys Val Thr Glu Asn Trp Ile Ser Ala
        35                  40                  45

Thr Leu Leu Leu Thr Pro Val Val Gly Thr Tyr Gln Tyr Ala Met
            50                  55                  60

Trp Tyr Lys Glu Gln Glu Lys Leu Ser His Arg Tyr
65                  70

<210> SEQ ID NO 9
<211> LENGTH: 824
<212> TYPE: DNA
<213> ORGANISM: Homo sapiens
<220> FEATURE:
<221> NAME/KEY: misc_feature
<223> OTHER INFORMATION: Incyte ID No: 1676225CB1

<400> SEQUENCE: 9
cggctcgagc ggctcgagcg ggaacccgga gcgctaagga gaacggacct cagaggttgt      60
ctgaaggccg aggccaagat ggcggtgctg tcagctcctg gcctgcgcgg cttccggatc     120
cttggtctgc gctccagcgt gggcccggct gtgcaggcac gaggtgtcca tcagagcgtg     180
gccaccgatg gccaagcag cacccagcct gccctgccaa aggccagagc cgtggctccc     240
aaacccagca gccggggcga gtatgtggtg gccaagctgg atgacctcgt caactgggcc     300
cgccggagtt ctctgtggcc catgaccttc ggcctggcct gctgcgccgt ggagatgatg     360
cacatggcag caccccgcta cgacatggac cgctttggcg tggtcttccg cgccagcccg     420

```
cgccagtccg acgtcatgat cgtggccggc acactcacca acaagatggc cccagcgctt      480
cgcaaggtct acgaccagat gccggagccg cgctacgtgg tctccatggg gagctgcgcc      540
aacggaggag gctactacca ctattcctac tcggtggtga ggggctgcga ccgcatcgtg      600
cccgtggaca tctacatccc aggctgccca cctacggccg aggccctgct ctacggcatc      660
ctgcagctgc agaggaagat caagcgggag cggaggctgc agatctggta ccgcaggtag      720
cgccgccgcc gccgccgccg agcctgtcg ccgtcctgtc cccagcctgc ttgtgtcccg       780
tgaggttgtc aataaacctg ccctcgggca aaaaaaaaa aaaa                        824
```

<210> SEQ ID NO 10
<211> LENGTH: 1113
<212> TYPE: DNA
<213> ORGANISM: Homo sapiens
<220> FEATURE:
<221> NAME/KEY: misc_feature
<223> OTHER INFORMATION: Incyte ID No: 2057235CB1

<400> SEQUENCE: 10

```
gtgacctagg accggctcac cgggtcgctt ggtggctccg tctgtctgtc cgtccgcccg       60
cgggtgccat catggcggac gcggccagtc aggtgctcct gggctccggt ctcaccatcc      120
tgtcccagcc gctcatgtac gtgaaagtgc tcatccaggt gggatatgag cctcttcctc      180
caacaatagg acgaaatatt tttgggcggc aagtgtgtca gcttcctggt ctctttagtt      240
atgctcagca cattgccagt atcgatggga ggcgcgggtt gttcacaggc ttaactccaa      300
gactgtgttc gggagtcctt ggaactgtgg tccatggtaa agttttacag cattaccagg      360
agagtgacaa gggtgaggag ttaggacctg gaaatgtaca gaaagaagtc tcatcttcct      420
ttgaccacgt tatcaaggag acaactcgag agatgatcgc tcgttctgct gctaccctca      480
tcacacatcc cttccatgtg atcactctga gatctatggt acagttcatt ggcagagaat      540
ccaagtactg tggactttgt gattccataa taaccatcta tcgggaagag ggcattctag      600 gattttttcgc gggtcttgtt cctcgccttc taggtgacat cctttctttg tggctgtgta      660
actcactggc ctacctcgtc aatacctatg cactggacag tggggtttct accatgaatg      720
aaatgaagag ttattctcaa gctgtcacag gattttttgc gagtatgttg acctatccct      780
ttgtgcttgt ctccaatctt atggctgtca acaactgtg tcttgctggt ggatgccctc      840
cttactcccc aatatatacg tcttggatag actgttggtg catgctacaa aaagagggga      900
atatgagccg aggaaatagc ttatttttcc ggaaggtcgc ctttgggaag acttattgtt      960
gtgacctgaa aatgttaatt tgaagatgtg gggcagggac agtgacattt ctgtagtccc     1020
agatgcacag aattatggga gagaatgttg atttctatac agtgtggcgc gctttttaa     1080 taatcattta atcttgggaa aaaaaaaaa aaa                                   1113
```

<210> SEQ ID NO 11
<211> LENGTH: 1712
<212> TYPE: DNA
<213> ORGANISM: Homo sapiens
<220> FEATURE:
<221> NAME/KEY: misc_feature
<223> OTHER INFORMATION: Incyte ID No: 2186363CB1

<400> SEQUENCE: 11

```
cttcatgcca ctgaagcaga tgatgtaccc tggcgtggcc cagagcatca acagtgatgt       60
caacaacctc atggccgtgt tgaacatgag caacatgctt ccagaaggcc tgttccccga      120
```

-continued

| | |
|---|---|
| gcacctgatc gacgtgctga ggcgggagct ggccctggag tgtgactacc agcgagaggc | 180 |
| cgcctgtgcc cgcaagttca gggacctgct gaagggccac cccttcttct atgtgcctga | 240 |
| gattgtggat gagctctgca gcccacatgt gctgaccaca gagctggtgt ctggcttccc | 300 |
| cctggaccag gccgaagggc tcagccagga gattcggaac gagatctgct acaacatcct | 360 |
| ggttctgtgc ctgagggagc tgtttgagtt ccacttcatg caaacagacc ccaactggtc | 420 |
| caacttcttc tatgaccccc agcagcacaa ggtggctctt ttggattttg gggcaacgcg | 480 |
| ggaatatgac agatccttca ccgacctcta cattcagatc atcagggctg ctgccgacag | 540 |
| ggacaggag actgtgcggg cgaaatccat agagatgaag ttcctcaccg gctacgaggt | 600 |
| caaggtcatg gaagacgccc acttggatgc catcctcatc ctgggggagg ccttcgcctc | 660 |
| tgatgagcct tttgattttg gcactcagag caccaccgag aagatccaca acctgattcc | 720 |
| cgtcatgctg aggcaccgtc tcgtcccccc acccgaggaa acctactccc tgcacaggaa | 780 |
| gatgggggc tccttcctca tctgctccaa gctgaaggcc cgcttcccct gcaaggccat | 840 |
| gttcgaggag gcctacagca actactgcaa gaggcaggcc cagcagtagg gctgcgggcc | 900 |
| acgcccaggc cggctccgcg ggaactctct ccctcagaca ggccaaaaac cagtagcgag | 960 |
| gtcgtggtga tgctcttttt aactcctttg cccaataagg ggggtggctg cctggagccc | 1020 |
| cgtagccagc gctttccacg gtttctgttg ctaaatggtt gtagggtgag aagtgcaaga | 1080 |
| atgaagatga agccccactg ctcggtcagt ctgcctccgt gtgtcctctg aaataagcag | 1140 |
| atgaagatga aagggcaact ttgttttctt ctttttcctg atgtgaatgt taagcagaag | 1200 |
| ggagagagtc cttactccct tccaatctct gttcagtgca aacccagaa acatgaacag | 1260 |
| atacgattgt gggattttta tcatctgtgt agtaggtgtg tgtatgtgtt ctagagtga | 1320 |
| gatttgtgtt ttctgccctt ttcctctcca gccgatgggc tggagctggg agaggtgctg | 1380 |
| agctaacagt gccaacaagt gctccttaag cctgcgaggc ccaggcctgt ggggctggtt | 1440 |
| ctcacctttg acagctgaat gttcctaaag aactgctgcc ccacagtgag ggtgggagca | 1500 |
| gcggaacagg gaatgccaga cacaggctcg ctgctgctgg aaggcggggt gggacttcct | 1560 |
| tcctctgtcc ggagaggcac aggtgtcacc agttccagcc aaaggctcct cacaggcgct | 1620 |
| gtgaatttt gtacaagtct tgtaattatc gaatcaacaa cttgtttcaa tttaataaaa | 1680 |
| atgctcatgg gaagtgcaaa aaaaaaaaaa aa | 1712 |

<210> SEQ ID NO 12
<211> LENGTH: 741
<212> TYPE: DNA
<213> ORGANISM: Homo sapiens
<220> FEATURE:
<221> NAME/KEY: misc_feature
<223> OTHER INFORMATION: Incyte ID No: 3126833CB1

<400> SEQUENCE: 12

| | |
|---|---|
| cacccaggta agaagaggcc gctcttcctg gggttgtttc tccgtgtgac gtgtggcctt | 60 |
| tgagatcaac tctcctgtac cagcgtaggc cgcatgagtg gggggcgggc tcccgcggtc | 120 |
| ctgctcggcg gagtggcctc tctgctcctg tcttttgttt ggatgccggc gctgctgcct | 180 |
| gtggcctccc gccttttgtt gctaccccga gtccttgctga ccatggcctc tggaagccct | 240 |
| ccgacccagc cctcgccggc ctcggattcc ggctctggct acgttccggg ctcggtctct | 300 |
| gcagcctttg ttacttgccc caacgagaag gtcgccaagg agatcgccag ggccgtggtg | 360 |
| gagaagcgcc tagcagcctg cgtcaacctc atccctcaga ttcatccat ctatgagtgg | 420 |

```
aaagggaaga tcgaggaaga cagtgaggtg ctgatgatga ttaaaaccca aagttccttg      480
gtcccagctt tgacagattt tgttcgttct gtgcacccctt acgaagtggc cgaggtaatt     540
gcattgcctg tggaacaggg gaactttccg tacctgcagt gggtgcgcca ggtcacagag      600
tcagtttctg actctatcac agtcctgcca tgatgagccc tgttcctgct catcatgaag      660
atccccgcga tacttcaacg ccttctgact tccaggtgat gactgggccc ccaataaatc     720
ccgtctttgg gaaaaaaaaa a                                                741
```

<210> SEQ ID NO 13
<211> LENGTH: 1759
<212> TYPE: DNA
<213> ORGANISM: Homo sapiens
<220> FEATURE:
<221> NAME/KEY: misc_feature
<223> OTHER INFORMATION: Incyte ID No: 3446038CB1

<400> SEQUENCE: 13

```
gaggaagatg cgaccggcag acggcattcg ctgggaacga cggatagact gggggctgcg      60
gcctagaggt ccgggcttgg agttcgcctc agacgcggtg gagccgccgg agtctgagaa     120
ggtcttcagg caccatggag gacaaacgca acatccagat catcgagtgg gaacacctgg     180
acaagaagaa gttctacgtg tttggtgtgg caatgacaat gatgatccgt gtcagtgtct     240
acccattcac cctcatccgc acccggttgc aagttcagaa ggggaagagc ctctaccatg     300
ggaccttcga tgccttcatc aagatcctgc gagcagatgg tatcactggc ctctaccgag     360
ggttcctggt caataccttc accctcatct ctggccagtg ttatgtcacc acttatgagc     420
tcacccggaa gtttgtagct gactacagcc agagtaacac agtcaaatca ctggtggctg     480
gtggctcagc ctcccttgtg gcccagagca tcacagtgcc cattgatgta gtctcccagc     540
acctgatgat gcaacgcaag ggtgagaaaa tgggccgctt tcaggtgcgg gggaactcag     600
agggacaagg ggtagttgcc tttggccaaa ccaaggacat catcaggcag atcctgcagg     660
ctgatggact tcgcggcttc tatcgaggct atgtggcttc actgcttacc tatatcccaa     720
acagtgctgt ctggtggccc ttctatcact tctatgcaga gcagctctcc tacctgtgtc     780
ctaaggagtg ccctcacatt gtctttcaag ctgtctcggg gccectggct gcagccactg     840 cctccatcct caccaatccc atggatgtca tacgaacccg tgtgcaggtt gagggcaaga     900
actccatcat cctgaccttc agacagctga tggcagaaga agggccttgg ggcctcatga     960
agggcctctc ggccagaatc atctcagcca accttccac cattgtcatt gtggtgggct     1020
atgagagcct caagaaactc agcctccgac ctgagctggt ggactcgaga cactggtaac     1080
cagtggtggg gagagaagcc tgctgttttc cacactaccg tgggtcaggg gcagagtgga     1140
gaggacagca ccctctccag gtgctcccac cacacaccca gccctgccct gggccaagtg     1200
gcctatctgg gatagggata gagactttga actgctcttg ctgaagaggc tccacgcctg     1260
gatcccttgc ccccactatt taaaattctc ttctgagctg ggctccctca ctcagtccct     1320
gtatttgata ctggcctaaa gaccccaccc cccaccctgc cagcccttct tctggcttcc     1380
ccttccatct gtgtccctga gaccctgaga agagctgtac atagagcttg cttactacca     1440
ctggttcttc ctcttgggct ttcagcccag actccaagca gctgctatca accctctctc     1500
ccttcatctc ttagccttgc ttatttttat tttgggaccg agctgcccac tagatgactc     1560
tgcttttccc tgcatttggg gctaaggtgc caggtactta tttgcacagg gagcaggagc     1620
agcaaaaaat ctctggttct ccagagcact cgtcctctct ttgagggggt tattaggttg     1680
```

```
ggagaaatgt tgatactttt gatttgtgtg tgtgtgtgtg tgtgtgagag tgtgtgtgtg    1740
tgtttggtaa acacatgtg                                                 1759

<210> SEQ ID NO 14
<211> LENGTH: 2188
<212> TYPE: DNA
<213> ORGANISM: Homo sapiens
<220> FEATURE:
<221> NAME/KEY: misc_feature
<223> OTHER INFORMATION: Incyte ID No: 4113161CB1

<400> SEQUENCE: 14
cggacgcgtg ggtgcttagc aacgggggga ggcaatgtgg ctgaaggtgg ggggcctact      60 tcggggacc ggtggacagc tgggccagac tgttggttgg ccttgtgggg ccctggggcc     120
tgggccccac cgctggggac catgtggagg ttcttgggcc caaaagtttt accaggatgg    180
gcctgggaga ggcctgggtg aggaggacat tcgcagggca cgggaggccc gtcccaggaa    240
gacaccccgg ccccagctga gtgaccgctc tcgagaacgc aaggtgcctg cctcccgcat    300
cagccgcttg gccaactttg ggggactggc tgtgggcttg gggctaggag tactggccga    360
gatggctaag aagtccatgc caggaggtcg tctgcagtca gaggtggtt ctgggctgga     420 ctccagcccc ttcctgtcgg aggccaatgc cgagcggatt gtgcagacct tatgtacagt    480
tcgaggggcc gccctcaagg ttggccagat gctcagcatc caggacaaca gcttcatcag    540
ccctcagctg cagcacatct ttgagcgggt ccgccagagc gccgacttca tgccccgctg    600
gcagatgctg agagttcttg aagaggagct cggcaggac tggcaggcca aggtggcctc      660
cttggaggag gtgccctttg ccgctgcctc aattgggcag gtgcaccagg gcctgctgag    720
ggacgggacg gaggtggccg tgaagatcca gtaccccggc atagcccaga gcattcagag    780
cgatgtccag aacctgctgg cggtactcaa gatgagcgcg gccctgcccg cgggcctgtt    840
tgccgagcag agcctgcagg ccttgcagca ggagctggct tgggagtgtg actaccgtcg    900
tgaggcggct tgtgcccaga atttcaggca gctgctggca aatgacccct tcttccgggt    960
cccagccgtg gttaaggagc tgtgcacgac acgggtgctg ggcatggagc tggctggagg   1020
ggtccccctg gaccagtgcc agggcctaag ccaggacctg cggaaccaga tttgcttcca   1080
gctcctgacg ctgtgtctgc gggagctgtt tgagttccga ttcatgcaga ctgaccccaa   1140
ctgggccaac ttcctgtatg atgcctccag ccaccaggtg accctgctgg actttggtgc   1200
aagccgggag tttgggacag agttcacaga ccattacatc gaggtggtga aggctgcagc   1260
tgatggagac agagactgtg tcctgcagaa gtccagggac ctcaaattcc tcacaggctt   1320
tgaaaccaag gcattctccg acgcccacgt ggaggcagtg atgatcctgg gggagccttt   1380
cgccacccag ggcccttatg actttgggtc gggggaaacg gcccgccgca tacaggacct   1440
catcccggtg ctgctgcggc accggctgtg tccccaccc gaggagacct atgccctgca    1500
ccgcaagctg gcaggggctt tcctggcctg tgcccacctc cgagcccaca tcgcctgcag   1560
ggacctcttc caggacacct accaccgcta ctgggccagt cgccagccag acgcagccac   1620
tgccggcagc ctccccacca aggggactc ctgggtggat cctcatgac agcctccatg      1680 ggggattcag tccccagagc aggccgtacc ctgctgtagt gcctcttatc ccttccccgt   1740
ctgccctggg tcagaggagc ccccttgggc ttccagtct tgcctggctc tcctccttgg     1800
cccaggagct caggatccct ggggctgggg aactcccaac ttcgtgccct agatcctgca   1860
cctccccact cgaaagtggg tatccgaaaa ctaagccagg gaagcggtta acttatcttt   1920
```

-continued

```
gccaacattt gagggagcct tgggccgctg catgtcgtta tgcagatcag actcatcagg      1980
gggagccctc acctctgcct caagcctccc gtggaaggcg agatggtcct ggaggcagtc      2040
ctcacctctg cctccctcgc tcctccaaca gctgccttct cccgggttcc agcctctcag      2100
tgtgttggag aggtaggggt gcggggtggg ggggagctga atcttcaatc ggaataaaag      2160
cagccctccc cttaaaaaaa aaaaaaaa                                         2188

<210> SEQ ID NO 15
<211> LENGTH: 488
<212> TYPE: DNA
<213> ORGANISM: Homo sapiens
<220> FEATURE:
<221> NAME/KEY: misc_feature
<223> OTHER INFORMATION: Incyte ID No: 4408678CB1

<400> SEQUENCE: 15
cagcgagcga gagcagcaca cacgcagcta gctaggagca gcagcagagc agcggcgatg        60
gcggcctcca tgatctcctc gtcagctctg gcggtggcgc ctcagggcct gccgcccctc       120
ggccgccgcg cctcctcctt cgccgtcgtc tgctccaaga agaagatcaa gaccgacaag       180
ccctacggga ttgggggtgg cctgaccgtc gacgtcgacg ccaacgggag aaagggcaag       240
ggcaaaggcg tgtaccagtt cgtcgacaag tacggcgcga acgtcgacgg atacagccca       300
atctacaacg aggatgactg gtctcccacc ggcgacgtct acgtcggtgg aaccactggg       360
cttctgatct gggccgtcac cctcgctggg atcctcggcg gcggcgccct cctcgtctac       420
aacaccagcg ccctctccgg ctaaggatat ccaatgcatg cgcttcttgc gattcgtcat       480
gtaaaatc                                                               488

<210> SEQ ID NO 16
<211> LENGTH: 473
<212> TYPE: DNA
<213> ORGANISM: Homo sapiens
<220> FEATURE:
<221> NAME/KEY: misc_feature
<223> OTHER INFORMATION: Incyte ID No: 4942111CB1

<400> SEQUENCE: 16
caccggcgac gcggggggaa catggggaag acgccggtgc ggatgaaggc ggtcgtgtac        60
gcgctgtcgc ccttccagca gaaggtaatg ccggggctgt ggaaggacat caccaccaag       120
atccaccaca aggtcaccga gaactggatc tccgccacgc tcctcctcac ccccgtcgtc       180
ggcacctacc aatacgccat gtggtacaag gagcaggaga agctttccca cagatattaa       240
atgcgctgcc cttgacagac agcactcgga gttttcatga tgggtttcat aatcctccca       300
tgatgattta acatttgttt gatcaatttc agttcaacgc ctttcatcg ttccatatgc       360 atatatggta tccgtgtctg gcaaacttat tttgaggctt gctaaatatg tacctttgt       420 ctctgaagtt gttaaataaa gcaaattaac ttccagttaa aaaaaaaaa aaa              473
```